(12) United States Patent
Spurgeon

(10) Patent No.: US 11,390,954 B2
(45) Date of Patent: Jul. 19, 2022

(54) MULTI-STEP PROCESS AND SYSTEM FOR CONVERTING CARBON DIOXIDE TO MULTI-CARBON PRODUCTS

(71) Applicant: UNIVERSITY OF LOUISVILLE RESEARCH FOUNDATION, INC., Louisville, KY (US)

(72) Inventor: Joshua Spurgeon, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 16/959,561

(22) PCT Filed: Dec. 31, 2018

(86) PCT No.: PCT/US2018/068117
§ 371 (c)(1),
(2) Date: Jul. 1, 2020

(87) PCT Pub. No.: WO2019/136018
PCT Pub. Date: Jul. 11, 2019

(65) Prior Publication Data
US 2021/0079537 A1 Mar. 18, 2021

Related U.S. Application Data

(60) Provisional application No. 62/612,843, filed on Jan. 2, 2018.

(51) Int. Cl.
| | | |
|---|---|---|
| C07C 11/00 | (2006.01) | |
| C07C 31/08 | (2006.01) | |
| C25B 3/00 | (2021.01) | |
| C25B 3/25 | (2021.01) | |
| C25B 9/70 | (2021.01) | |
| B01J 23/50 | (2006.01) | |
| B01J 23/72 | (2006.01) | |
| C07C 11/04 | (2006.01) | |
| C07C 31/10 | (2006.01) | |
| C07C 31/12 | (2006.01) | |
| C07C 47/06 | (2006.01) | |
| C07C 53/08 | (2006.01) | |
| C07C 53/124 | (2006.01) | |
| B82Y 99/00 | (2011.01) | |

(52) U.S. Cl.
CPC .............. *C25B 3/25* (2021.01); *B01J 23/50* (2013.01); *B01J 23/72* (2013.01); *C07C 11/04* (2013.01); *C07C 31/08* (2013.01); *C07C 31/10* (2013.01); *C07C 31/12* (2013.01); *C07C 47/06* (2013.01); *C07C 53/08* (2013.01); *C07C 53/124* (2013.01); *C25B 9/70* (2021.01); *B82Y 99/00* (2013.01)

(58) Field of Classification Search
CPC ......... C07C 11/04; C07C 31/08; C07C 31/10; C25B 3/26
See application file for complete search history.

(56) References Cited

U.S. PATENT DOCUMENTS

| | | | |
|---|---|---|---|
| 9,315,910 B2* | 4/2016 | Eastman | C10G 2/50 |
| 2009/0014336 A1 | 1/2009 | Olah et al. | |
| 2012/0018311 A1 | 1/2012 | Yotsuhashi et al. | |
| 2012/0329657 A1 | 12/2012 | Eastman et al. | |
| 2013/0175181 A1 | 7/2013 | Kaczur | |

FOREIGN PATENT DOCUMENTS

WO 2016/178590 A1 11/2016

OTHER PUBLICATIONS

Hsieh et al.; "Effect of Chloride Anions on the Synthesis and Enhanced Catalytic Activity of Silver Nanocoral Electrodes for CO2 Electroreduction"; ACS Catalysis, 2015, vol. 5, No. 9, pp. 5349-5356.

* cited by examiner

*Primary Examiner* — Sikarl A Witherspoon
(74) *Attorney, Agent, or Firm* — WCF IP

(57) ABSTRACT

Systems and methods for the electrochemical conversion of COT to multi-carbon products are provided. Each system and method comprises a sequence of multiple, independently optimized electrochemical reaction steps that take place in separate reaction chambers.

24 Claims, 12 Drawing Sheets

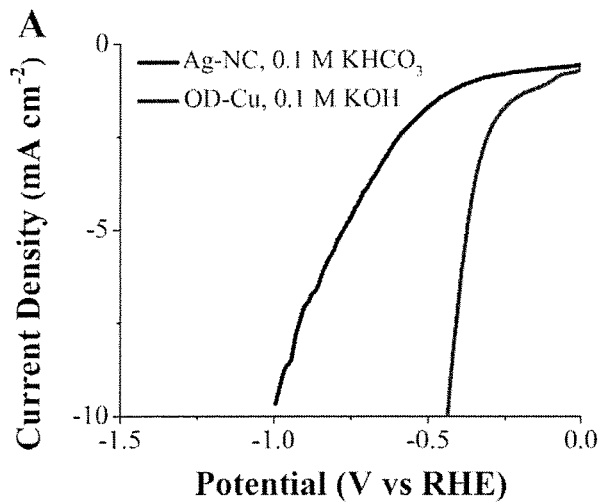
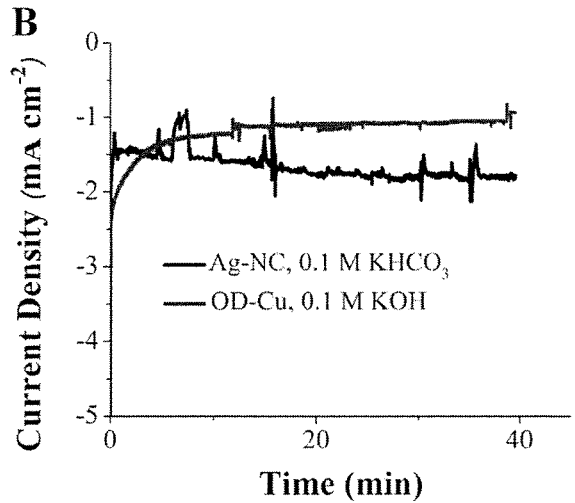
Figure 7A
Figure 7B
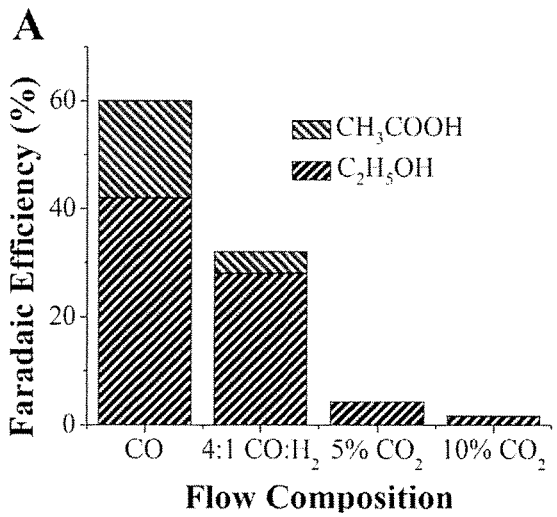
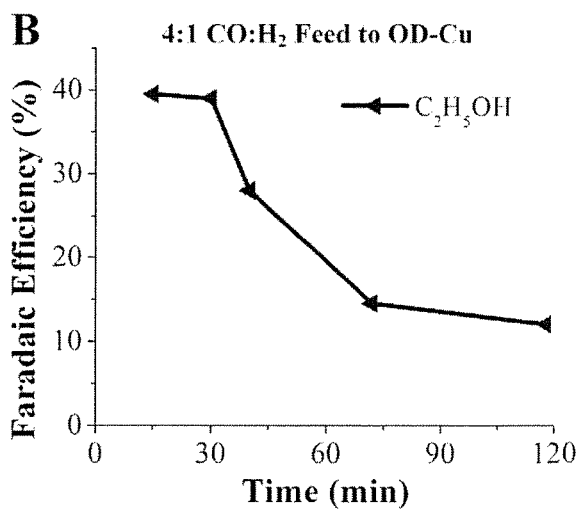
Figure 8A
Figure 8B

MULTI-STEP PROCESS AND SYSTEM FOR CONVERTING CARBON DIOXIDE TO MULTI-CARBON PRODUCTS

BACKGROUND OF THE INVENTION

Field of the Invention

The invention generally relates to improved systems for and methods of converting a starting material with a low carbon number (e.g. $CO_2$) to multi-carbon products such as multi-carbon alcohols. In particular, the invention provides integrated systems and methods for the electrochemical conversion of reactants with a low carbon number (e.g. $CO_2$) to multi-carbon products using a sequence of multiple, independently optimized reaction steps, each of which is performed in a separate reaction module.

Description of Related Art

The reduction of carbon dioxide with water to produce hydrocarbons is a feasible process to accomplish energy storage at the terawatt scale. Liquid hydrocarbons such as ethanol have the advantage of a high volumetric energy density (24 MJ/L for $C_2H_5OH$) which is greater than compressed $H_2$ or the most advanced battery technologies. Furthermore, electrolytic $CO_2$ reduction to fuels is a carbon-neutral process, contributing to sustainability and mitigating climate change. Even lightweight liquid hydrocarbons have relatively favorable energies per volume, e.g. methanol (15.6 MJ/L) and ethanol (24 MJ/L). The $CO_2$ feedstock for fuel production is available in concentrated form as an unwanted byproduct from the flue stacks of numerous industrial processes. Further, many different products are possible in the carbon dioxide reduction reaction ($CO_2RR$) coupled with the oxidation of water.

The reactions for typical $CO_2RR$ products range from a 2-electron process for carbon monoxide to a 12-electron process for ethanol. Although the thermodynamic potentials for these reactions can be overcome with modest applied voltage, there are considerable kinetic barriers to the conversion of $CO_2$ to more complex products. The kinetic limitations, which arise from the multiple proton-coupled electron transfer steps required for the conversion, lead to large overpotentials during $CO_2RR$ electrolysis.

Most electrocatalysts only yield $C_1$ products, but copper surfaces are capable of directing significant faradaic current to C—C bond forming reactions and producing $C_2$ and $C_3$ products. While there has been success at achieving high yields of CO and formate in a single-step $CO_2$ reduction process, more energy-dense fuel products such as methanol, ethanol, etc. have been limited to much lower faradaic efficiencies and typically required high overpotentials. The myriad possible reaction pathways on the way to $C_2$ and $C_3$ compounds underscores the difficulty of achieving high product selectivity in a single reaction step. Therefore, the field of electrolytic $CO_2$ reduction would benefit greatly from the development of approaches and systems to influence the selectivity of inorganic heterogeneous catalysts to more complex, desirable fuel products.

One possible approach to directing $CO_2$ reduction toward a more energy-dense product in high yield is to break down a complex electron-transfer reaction requiring many electrons into multiple reaction steps with fewer electron transfers per step and relatively stable products. In this type of "one-pot cascade catalysis", the products of the first reaction become the reactants of the second reaction, and so on, allowing for the design of multiple catalysts to minimize the activation barrier of each intermediate reaction on the way to the end product. However, one major difficulty with this approach has been identifying multiple compatible catalysts that operate effectively under the same reaction conditions and are not poisoned by any of the intermediates.

In addition, electrocatalysts generally suffer from high overpotential and poor selectivity for multi-carbon products such as ethanol. In order to encourage a specific reaction pathway with low overpotentials, typically the rate-limiting intermediate step is identified and its binding energy is optimized so that it occurs at a low potential preferentially to other possible pathways. However, a catalyst change which alters the binding energy of a specific intermediate step has the likely concomitant effect of changing the binding energy of the other intermediate steps. This limits the ability to tune a single electrocatalyst surface for the optimization of a multi-electron-transfer reaction. This limitation is known as the scaling relation, and is a major challenge in the field of heterogeneous electrocatalysis.

Catalytic advances are strongly needed to improve the prospects of this technology.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

The present disclosure describes a rational, modular approach to the conversion of a starting material with a low carbon number such as $CO_2$ to multi-carbon products, in particular energy-dense fuels such as multi-carbon alcohols. The systems and methods were developed by taking into account the reaction mechanisms of the individual steps leading from e.g. $CO_2$ to particular multi-carbon products. The conversion advances by a series of sequential, single, proton-coupled electron-transfer steps, each of which takes place in a separate reaction module (compartment, chamber, etc.). Within a module, reaction conditions, including the type of electrode, electrolyte, etc. are optimized for one reaction of a multi-step reaction pathway.

This compartmentalized system thus does not suffer from the scaling relation problems of the prior art. Instead, a $CO_2RR$ mechanistic pathway, which would otherwise be branched, is purposefully directed so as to optimize a single intermediate step in each module. Different catalysts with different binding energies may be employed in each module, and variables such as temperature, potential, pH, catalyst surface structure, and others are adjusted (tuned, optimized) to further differentiate/optimize reaction conditions for each reaction. The individually optimizable reactions of this sequential cascade system thus provide distinct advantages compared to prior art systems and methods, particularly with respect to avoiding or lessening the branching of the $CO_2$ reduction pathway and preventing formation of a plurality of complex, multi-carbon products in a single reaction and/or producing unwanted species.

It is an object of this invention to provide a method of electrochemical conversion of $CO_2$ to a multi-carbon compound comprising: in a first reaction module, reacting $CO_2$ with water under first electrochemical reaction conditions sufficient to produce CO and hydroxide ions; transferring the CO to a second reaction module; in the second reaction module, reacting the CO with water under second electrochemical reaction conditions sufficient to produce the multi-carbon compound; and collecting the multi-carbon compound. In some aspects, the first electrochemical reaction conditions differ from the second electrochemical reaction conditions. In other aspects, the first electrochemical reaction conditions include the use of a first catalyst and the second electrochemical reaction conditions include the use of a second catalyst. In additional aspects, the first catalyst and the second catalyst are different. In further aspects, the multi-carbon compound is a multi-carbon alcohol, a multi-carbon hydrocarbon, a multi-carbon aldehyde or a multi-carbon carboxylic acid; and in yet further aspects, the multi-carbon alcohol is ethanol, propanol, or butanol. In some aspects, the multi-carbon hydrocarbon is ethylene. In other aspects, the multi-carbon aldehyde is acetaldehyde or propionaldehyde. In yet other aspects, the multi-carbon carboxylic acid is acetic acid or gamma-hydroxybutyric acid. In further aspects, the multi-carbon alcohol is ethanol; the first electrochemical reaction conditions include contacting the $CO_2$ and water with an Ag-based catalyst or an Au-based catalyst, and the second electrochemical reaction conditions include contacting the CO and water with an oxide-derived Cu catalyst, a nanostructured Cu catalyst or a heteroatomic carbon based catalyst. In some aspects, the Ag-based catalyst is Ag-nanocoral (Ag—NC). In other aspects, the oxide-derived Cu catalyst is an oxide-derived nanocrystalline copper complex (OD-Cu) catalyst.

The invention also provides a modular system for the electrochemical conversion of carbon dioxide to a multi-carbon alcohol, comprising: a first electrolyzer module comprising a first catalyst that catalyzes the conversion of $CO_2$ to CO; a second electrolyzer module comprising a second catalyst that catalyzes the conversion of CO to a multi-carbon compound; a conduit for transferring CO from the first electrolyzer module to the second electrolyzer module. In some aspects, the first and second catalysts are different. In other aspects, reaction conditions in the first electrolyzer module differ from reaction conditions in the second electrolyzer module. In further aspects, the first catalyst is an Ag-based catalyst or an Au-based catalyst, and the second catalyst is an oxide-derived Cu catalyst, a nanostructured Cu catalyst, a heteroatomic carbon-based catalyst or a doped nanodiamond-based catalyst. In additional aspects, the Ag-based catalyst is an Ag-nanocoral (Ag—NC) catalyst. In some aspects, the oxide-derived Cu catalyst is an oxide-derived nanocrystalline copper complex (OD-Cu) catalyst. In other aspects, a $CO_2$ absorption column is operably connected to the first electrolyzer module, wherein the $CO_2$ absorption column supplies $CO_2$ to the first electrolyzer module.

In yet further aspects, a gas-liquid separator is disposed between the first electrolyzer module and the second electrolyzer module, wherein the gas-liquid separator i) separates CO and electrolyte from a CO-electrolyte stream received from the first electrolyzer module; ii) transfers the CO to the second electrolyzer module; and e) transfers the electrolyte back to the first electrolyzer module.

BRIEF DESCRIPTION OF THE DRAWINGS

FIGS. 7A and B. Two-stage cascade performance. (A) Current density vs. potential for the first-stage (black curve) and second-stage (red curve) electrolyzers. (B) Current density vs. time for cascade at potentiostatic operating conditions with the first cell at −0.6 V vs. RHE and the second cell at −0.3 V vs. RHE.

FIGS. 8A and B. (A) Liquid product faradaic efficiencies for the second electrolyzer with varying flow composition. 5% and 10% $CO_2$ compositions had a balance of 4:1 CO:$H_2$. (B) Second electrolyzer liquid product faradaic efficiency vs. time with a 4:1 CO:$H_2$ feedstock.

DETAILED DESCRIPTION

Figure 1:
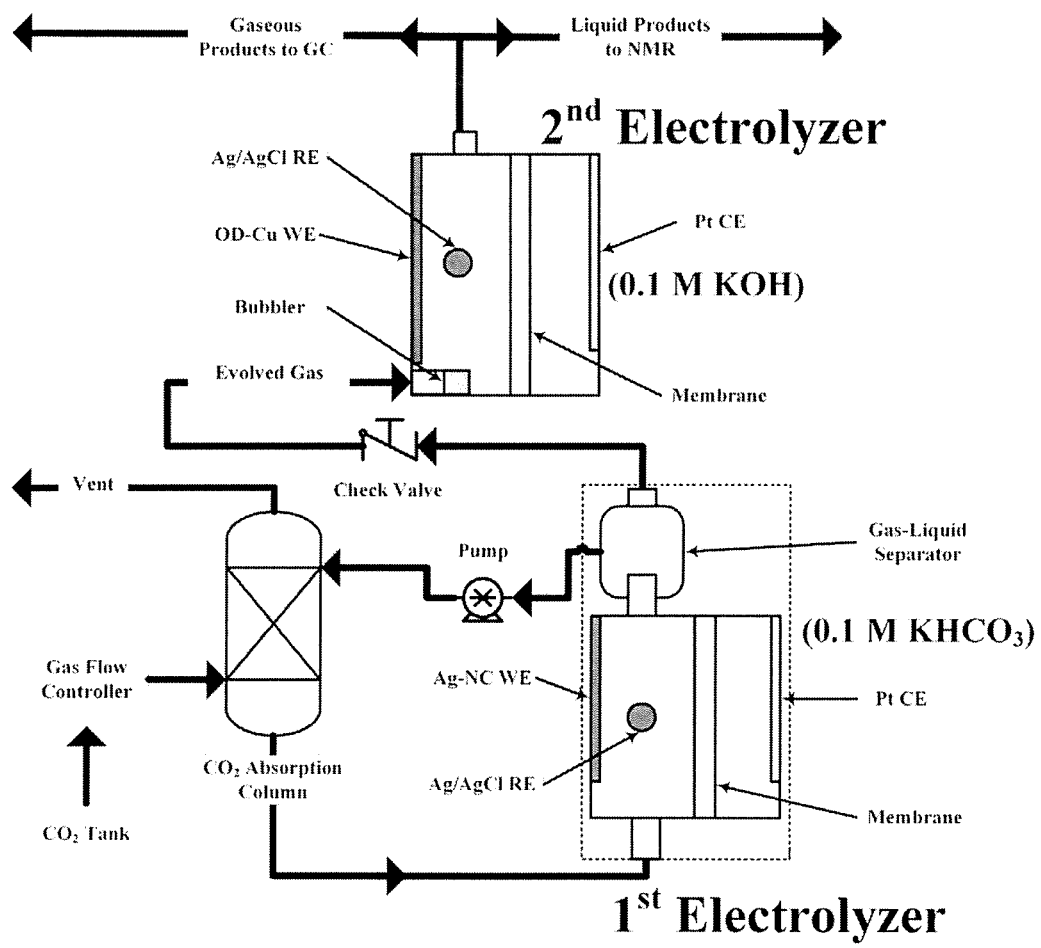
FIG. 1. Detailed schematic of an exemplary two-step $CO_2$-to-ethanol cascade electrolysis system.

Described herein are methods, systems, and devices for electrochemically converting a starting material with a low carbon number, such as $CO_2$, into one or more multi-carbon compounds, e.g. multi-carbon alcohols. The systems and methods utilize an "assembly line" approach and involve the multistep electrocatalytic reduction of e.g. $CO_2$ to form multi-carbon products via a cascade of sequential reactions. Each reaction of the multistep pathway takes place in a separate reaction chamber or vessel (module) under conditions which are optimized for that specific reaction.

Definitions

"Electrolyte" as used herein refers to a chemical compound (e.g. a liquid or gel) that dissociates into ions and hence is capable of transporting electric charge, i.e. an electrolyte is an electric conductor. Unlike metals, in electroytes the flow of charge is not a flow of electrons but is a movement of ions. As used herein, a "catholyte" is the portion of an electrolyte which is on the cathode side of an electrochemical cell that is effectively divided into two compartments, such as those described herein. In other words, the catholyte is the portion of the electrolyte in the immediate vicinity of the cathode in an electrolytic cell. This is as opposed to the anolyte, which is the portion of an electrolyte which is on the anode side of an electrochemical cell.

As used herein, "electrocatalyst" refers to a catalyst that participates in electrochemical reactions. Electrocatalysts are a specific form of catalysts that function at electrode surfaces or are the electrode surface itself. The electrocatalyst assists in transferring electrons between the electrode and reactants, and/or facilitates an intermediate chemical transformation described by an overall half-reaction. An electrocatalyst can be heterogeneous, capable of catalyzing a plurality of reactions, or homogeneous capable of specifically catalyzing one or only a few related types of reactions.

"Electrode" refers to a solid electric conductor that carries electric current into non-metallic solids, or liquids, gases, plasmas, or vacuums. An electrochemical cell contains two types of electrodes: a cathode, at which reduction takes place, and an anode, at which oxidation reactions take place. The systems described herein include: a working electrode, i.e. a cathode, at which the cell reaction takes place; a counter (auxiliary) electrode (anode) to close the current circuit in the electrochemical cell; and, optionally, a reference electrode which establishes the electrical potential against which other potentials are measured, e.g. for laboratory testing purposes.

As used herein, a catalyst that is "derived" from a material is a catalyst that is "based" on the material (e.g. is made from and/or includes the material).

Reactions and Pathways

In order to practice the present methods, it is necessary to select a targeted multi-carbon compound for production and identify a pathway that is suitable for its production. The pathway generally must comprise discrete separable steps which can be performed sequentially. Each of the steps produces an intermediate of the pathway, except the last step which produces the final product. For a pathway to be feasible, the intermediates and the final product should be stable species that, once produced in a module, are unlikely to react further under the conditions in the module. Each intermediate and the final product should also be separable from the milieu in which each is created, e.g. separable from the electrolyte that is present in the reaction module and/or from other byproducts.

Multi-carbon compounds that may be synthesized using the methods described herein include but are not limited to: multi-carbon alcohols such as ethanol, propanol, butanol; multi-carbon hydrocarbons such as ethylene; multi-carbon aldehydes such as acetaldehyde, propionaldehyde; and multi-carbon carboxylic acid such as acetic acid and gamma-hydroxybutyric acid.

Examples of pathways that are used to synthesize the multi-carbon compounds described above include the following:

For ethanol, an exemplary pathway is $CO_2$ electroreduction to CO with Ag or Au based catalysts, followed by CO electroreduction to ethanol with oxide-derived or nanostructured Cu or heteroatomic carbon based catalysts.

For acetic acid, an exemplary pathway is $CO_2$ electroreduction to CO with Ag or Au based catalysts, followed by CO electroreduction to acetate with oxide-derived or nanostructured Cu forms or doped nanodiamond based catalysts.

For gamma-hydroxybutyric acid, an exemplary pathway is $CO_2$ electroreduction to CO with Ag or Au based catalysts, followed by CO electroreduction to gamma-hydroxybutyric acid with copper oxide and oxide-derived copper based catalysts at high CO flow rates.

Further descriptions of the catalysts employed in the pathways are provided below.

Optimization of Pathways

Once a targeted compound and a pathway to its synthesis are selected, the individual steps of the pathway are optimized e.g. to maximize yield and minimize overpotential, by considering several factors and/or adjusting several parameters. Generally, the steps are optimized using a combination of extant knowledge in the art and/or experimental data. Elements that are optimized include but are not limited to: electrolytes, catalysts and morphology; reaction temperature; applied bias; pH; gas flow rate; etc., as described in detail below. The goal of optimization for each of the steps is generally to achieve a high level of conversion of a starting material to a single product of interest (e.g. an intermediate or the end-product). However, in some cases, the production of low levels of unwanted by-products may be tolerated, especially if the desired product is separable from the unwanted by-products.

The results of selecting a particular group of parameters for a reaction is generally judged by comparing e.g. the yield of the desired end product, especially product maximization while minimizing overpotential (the potential difference [voltage] between a half-reaction's thermodynamically determined reduction potential and the potential at which the redox event is experimentally observed at a given current). Methods of measuring/quantifying yields are known and, depending on the compound, include but are not limited to HPLC, NMR, GC, mass spec, infrared spectroscopy, UV/vis, and other methods.

Electrodes/Catalysts

The "working electrodes" referred to herein are generally electrocatalysts and may be known commercially available catalysts or novel, custom made catalysts. Preferably, an electrocatalyst that is selected as a working electrode is specific or preferentially catalyzes the reaction that is performed in a single module. However, an electrocatalyst may be capable of catalyzing many different reactions, but in the absence of the conditions within a given module (e.g. available substrate, temperature, electrolyte, etc.) only one reaction, or a limited number of reactions, is/are available to be catalyzed, and/or only one reaction is preferentially catalyzed. For example, the catalyst may be capable of transforming a desired intermediate into a second, less or not desired intermediate, but does so at a much lower level, e.g. at less than about 50, 40, 30, 20 or 10% or less, of the level of production of the intermediate of choice that is to be transferred to the next module.

$CO_2$ conversion to multi-carbon products involves the formation of carbon-carbon bonds at one or more steps during the process. The C—C coupling requires a non-electrochemical step in which two adsorbed carbon species migrate to adjacent sites and react. C—C bond formation is believed to occur by reaction of hydrogenated adsorbed *CO species rather than $CO_2$. This step proceeds most easily when adsorbed *CO are hydrogenated and adsorbed in close proximity, i.e. at spatially adjacent sites.

One avenue for bringing adsorbed carbon species into more frequent contact is to nanostructure the catalyst surface and the use of catalysts with nanostructure surfaces is encompassed. In this method, 3D topography is used to place more active sites within reach of each other, thereby increasing the formation of C—C bonds. The catalyst metals are prepared with high-purity metals and intentional surface structuring is performed, for example, by nanoparticle synthesis, oxide-derived roughening (thermal oxidation followed by reduction under strongly cathodic potentials), or electrodeposition with an inhibitor to make a metallic foam.

The catalyst surface before and after extended electrochemical testing is imaged e.g. with scanning electron microscopy (SEM) to monitor feature sizes and any notable morphological changes. For nanoparticulate catalysts and nanostructured surfaces, transmission electron microscopy (TEM) is employed on tested and untested samples, characterizing particle or surface feature size, crystallinity, and faceting. Bulk crystallinity and surface orientation of catalyst films is established with x-ray diffraction (XRD). X-ray photoelectron spectroscopy (XPS) is used to characterize the chemical composition and oxidation state of the top few nm of the catalyst before and after $CO_2$ reduction experiments. These measurements can indicate whether or not a catalyst has been poisoned and with what type of molecule.

Electroreduction of $CO_2$ to CO

For a first step of converting $CO_2$ to CO, suitable catalysts include but are not limited to: Ag based or derived catalysts (i.e. catalysts that comprise Ag); Au based catalysts; Cu based catalysts; doped carbon catalysts; nickel-based catalysts; catalysts based on metal oxides; other metal-based catalysts; etc.

Examples of suitable Ag based catalysts include but are not limited to: Ag foils, Ag nanoparticles, Ag-nanocoral (Ag—NC), etc.

Examples of Au based catalysts include but are not limited to: Au foils and nanostructured Au.

Examples of Cu based catalysts include but are not limited to: nanostructured Cu examples of which include but are not limited to: Cu foam electrodeposited with 3,5-diamino-1,2,4-triazole inhibitor (CuDAT)); and Cu nanoparticles supported on e.g. B- or N-doped carbon (for example, supported on e.g. B- or N-doped graphene, nanotubes, nanofibers, nanodiamond, etc.).

Examples of doped carbon catalysts include but are not limited to B- or N-doped carbon (for example, supported on e.g. B- or N-doped graphene, nanotubes, nanofibers, nanodiamond, etc.).

Examples of nickel-based catalysts include but are not limited to nickel deposited on alumina.

Examples of catalysts based on metal oxides include but are not limited to catalysts based on iron oxide or chrominum oxide.

Electroreduction of CO

For a second step of converting CO to a desired product, exemplary catalysts are as follows:
1. Electroreduction to ethanol can be performed with e.g. oxide-derived Cu, nanostructured Cu, heteroatomic or doped carbon based catalysts, etc.

Examples of oxide-derived Cu catalysts include but are not limited to: B-doped oxide-derived-Cu.

Examples of nanostructured Cu catalysts include but are not limited to: Cu foam electrodeposited with 3,5-diamino-1,2,4-triazole inhibitor (CuDAT)); and Cu nanoparticles supported on e.g. B- or N-doped carbon (for example, supported on e.g. B- or N-doped graphene, nanotubes, nanofibers, nanodiamond, etc.).

2. Electroreduction to acetic acid can be performed with oxide-derived Cu, nanostructured Cu, heteroatomic (doped) carbon based catalysts such as doped nanodiamond based catalysts, etc. examples of which are listed above.
3. Electroreduction to gamma-hydroxybutyric acid, with copper oxide and oxide-derived copper based catalysts, examples of which are listed above.

Other catalysts that can be employed include, e.g. Sn nanostructures.

Interdigitated Electrodes

Figures 13A, 13B:
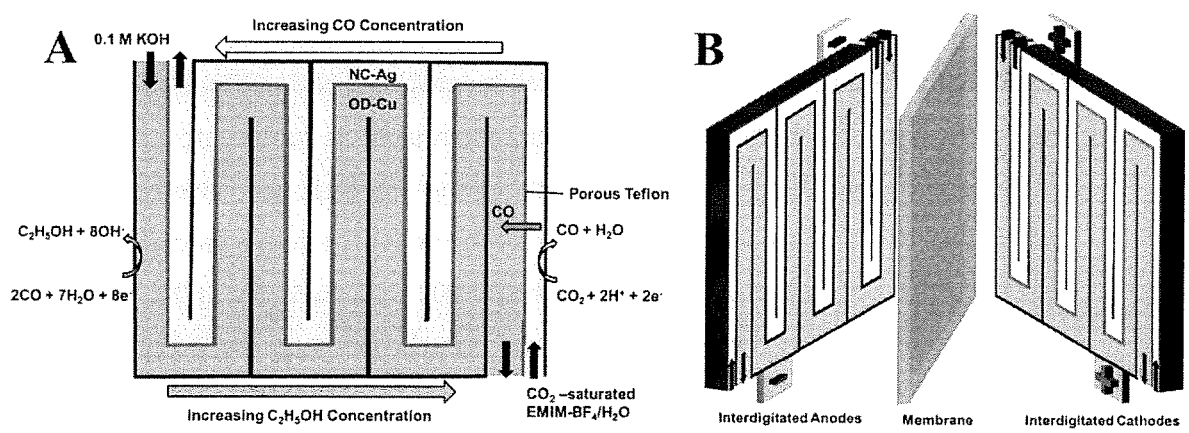
FIGS. 13A and B. Interdigitated electrode integrated cascade electrolyzer design. (A) Cathode of interdigitated serpentine flow fields with cascade stages separated by a porous Teflon wall. (B) Exploded view of the four-terminal integrated electrolyzer.

The disclosure also encompasses the use of electrocatalysts which are electrodes with an interdigitated design. In such electrodes, a recessed, serpentine path across the entire electrode surface is provided for the flow of an electrolyte. This design provides the maximum opportunity to build reactant concentration for a reaction and drive diffusion to a next-stage electrolyte. In this case, the first stage electrode is positioned on a porous membrane with the serpentine pathway facing the membrane, and a next (e.g. second) stage electrode is positioned on the opposite side of the porous membrane. The next stage electrode has a recessed, serpentine pathway through which an electrolyte suitable for the next reaction flows, and this serpentine pathway is also oriented to directly face the membrane. Further, in some aspects, the electrode is designed so that the next (second)-stage electrolyte flows in the opposite direction from the first stage electrolyte, ensuring the best possible concentration gradient across the porous membrane to transfer the product produced by the first reaction through the membrane and into the next electrode (e.g. see FIGS. 13A and B).

In some aspects, such interdigitated electrodes are produced as follows:
i) a recessed, non-linear (e.g. serpentine or curved pathway) is produced on the surface of two end plates, one of which functions as a substrate for containing elements necessary for catalyzing the first reaction, and the other of which functions as a substrate for containing elements necessary for catalyzing the second reaction. For example, a suitable metal is deposited on an end plate and then a non-linear (e.g. serpentine) groove is made in the deposited metal to separate the two stages of the cascade electrolyzer and define two channels on both the anode and cathode. Each channel has an inlet for receiving a reactant that is dissolved or suspended in an electrolyte, and an outlet through which spent electrolyte exits the channel (e.g. see FIGS. 13A and B). Between the inlet and the outlet, the path of the channel makes a plurality of turns and winds back and forth, increasing the surface area over which each portion of electrolyte flows. Suitable metals for depositions include but are not limited to: Ag, Ni, Au, etc. The metal is deposited, e.g. by evaporation, sputtering, ink methods, etc. Grooves are introduced into the metal layer by methods such as machine milling, laser etching, lithography and chemical etching. Suitable catalyst metals, such as Ag, Cu, Au, Sn are then selectively deposited (e.g. by electrodeposition) so as to isolate each metal to the serpentine channel defining one portion of the integrated electrolyzer electrode, before being further processed to e.g. Ag—NC and OD-Cu or other nanostructured surface. Example 3 provides an example of production.

The channels of each electrode are filled with a suitable electrolyte during operation and, for the cathode, the groove is filled with a permeable divider or wall (e.g. a porous Teflon membrane or nanoporous material such as anodic alumina or titania positioned between the interdigitated electrodes. The anode is produced in similar fashion but with an impermeable divider between the two electrodes.

Other Electrodes

Examples of electrocatalysts that are suitable for use in other reactions (reactions that are not C—C bond formation) include but are not limited to: Cu electrocatalysts (e.g. for the conversion of CO to ethanol); Rh electrocatalysts (e.g. for propionaldehyde formation from CO); etc.

In addition, the systems described herein optionally include at least one reference electrode which establishes the electrical potential against which other potentials are measured, e.g. for the purposes of studying reactions in the laboratory. Examples of suitable reference electrodes include but are not limited to: Ag/AgCl electrodes, saturated calomel electrodes (SCE), etc.

Selection of Various Components and Parameters

Selection of Electrolyte(s): Catholytes and Anolytes

The choice of catholyte is guided by one or more of many factors, including but not limited to: the type of reaction that is taking place, cost, environmental impact for disposal, reactant solubility, pH, carbonate stability, etc. For example, one factor is maximization of the solubility of one or more reactants, intermediates or products, or in some cases, minimizing the product solubility e.g. to promote gaseous separation to the next stage of the electrolysis. Examples of suitable catholytes include but are not limited to: aqueous sodium or potassium bicarbonate solution, aqueous alkaline sodium or potassium hydroxide, and ionic liquids with high $CO_2$ or CO solubility.

Some ionic liquids have very high $CO_2$ solubility, and have been shown to greatly reduce the overpotential for $CO_2$ conversion to CO by lowering the free energy of the $CO_2^-$ intermediate. Examples of these catholytes include but are not limited to: 1-ethyl-3-methylimidazolium tetrafluoroborate (EMIM-BF4).

Examples of suitable anolytes that may be employed in the systems described herein include but are not limited to: aqueous sodium or potassium bicarbonate solution, aqueous alkaline sodium or potassium hydroxide, and ionic liquids with high $CO_2$ or CO solubility.

Selection of Temperature

The choice of a temperature for conducting a particular reaction is typically made by one or both of reliance on extant art and experimental data. For example, the art may suggest a range of suitable temperatures, and a practitioner may conduct the reaction at several temperatures within the range (without undue experimentation) to determine those which are optimal. Temperature selection may also be based on practical criteria such as the equipment that is available, safety, etc.

For example, for the electrochemical conversion of $CO_2$ to CO, or CO to ethanol, a suitable range is 20-90° C. (based on, for example, maintaining proper function of the ionomer membrane). Usually the reactions are performed at about room temperature.

Selection of Applied Bias

The choice of a suitable applied bias for conducting a particular reaction is also typically made by one or both of reliance on extant art and experimental data. For example, the art may suggest a range of recommended values and a practitioner may, without undue experimentation, conduct the reaction at several that fall within the range to determine those which are optimal.

For example, for the conversion of $CO_2$ to CO a suitable range is −0.1 to −1.0 V vs. RHE at the cathode; for the conversion of CO to ethanol, a suitable range is −0.2 to −0.8 V vs. RHE; etc.

In some aspects, C—C bond formation is promoted by pulsing of the applied bias. Under potentiostatic conditions after two adsorbed carbon species merge into a C2 species and desorb, mass transport limitations of replacement carbon species to the active sites may not be able to keep up with electron-transfer, thus promoting $H_2$ formation or the further reduction of a C1 species. Pulsing the applied bias between a rest and working potential promotes C2 molecule formation and provides sufficient time for the adsorption and migration of new *CO species to adjacent active sites. The pulse method should permit more time for *CO species to occupy adjacent sites as well as allowing more time for additional CO to leave the first stage of reaction, leading to higher C2+ faradaic efficiencies.

For example, pulse times of about 1-10 seconds, e.g. 1, 2, 3, 4, 5, 6, 7, 8, 9, or 10 seconds of applied bias, such as about 3-5 seconds, with a rest period of about 1-10 seconds, e.g. 1, 2, 3, 4, 5, 6, 7, 8, 9, or 10 second of no applied bias, such as about 3-5 seconds, may be utilized.

Membranes

If compartments are present in a reactant module, a membrane, e.g. a permeable or selectively permeable membrane, is used to divide the module. The membrane prevents product species from oxidizing at the anode and thus promotes high yields. Types of membranes that can be used include but are not limited to: commercial anion-exchange or proton-exchange material, depending upon electrolyte pH, including ionomers such as Selemion and Nafion.

Sources of Reactants

In some aspects, the starting reactant is $CO_2$ which is subsequently converted to a multi-carbon compound. The $CO_2$ may come from any source. In some aspects, the $CO_2$ is advantageously "waste" $CO_2$ that would otherwise be released into the atmosphere. Notable sources of waste $CO_2$ include but are not limited to: power generating stations which burn fossil fuels such as coal, oil and natural gas; waste disposal practices, including landfilling, incineration, large scale composting etc.; commercial fermentation processes; cement manufacturing, etc. Any of these sources of $CO_2$ may be coupled or connected to the systems described herein, so as to transfer waste $CO_2$ to the systems, either directly or via an intermediate service that collects and distributes $CO_2$.

The systems and methods described herein are not limited to using $CO_2$ as the only reactant. Subsequent cascade electrolyzer could utilize mixed reactant inputs (e.g. for C3+ species formation). The rate of some mechanistic steps, particularly those involving C—C bond formation, are influenced by the relative concentrations of the adsorbed carbonaceous species. For example, additional high concentrations of CO can be used to drive the formation of C3+ species. In addition, the product streams of two reactors can be merged to provide a mixed reactant input that drives a desired reaction.

In particular, the results presented in the Examples below indicated by NMR that ethanol ($CH_3CH_2OH$) in the stationary second-stage catholyte was eventually converted to propionaldehyde ($CH_3CH_2CHO$) and other species such as aromatics. The present systems and methods can be modified toward production of these species, for example, by reacting varying concentrations of ethanol, acetaldehyde, propanol, and propionaldehyde as starting materials with and without controlled flow inputs of $CO_2$, CO, $H_2$, and $C_2H_4$ to achieve conversion to C3+ species, as listed above.

Exemplary Methods and Systems

The present disclosure provides multistep methods for converting a starting material with a low carbon number, e.g. (e.g. with 1, 2 or 3 carbons such as $CO_2$, CO, etc.) to at least one multi-carbon compound such as a multi-carbon alcohol.

As an example, in some aspects, the methods involve, in a first electrolyzer module, performing a first electrochemical step of converting $CO_2$ and water to CO and hydroxide ions by exposing the carbon dioxide and water to a first set of reaction conditions sufficient to form carbon monoxide and hydroxide ions. The first reaction conditions include exposing the $CO_2$ and water to a suitable catalyst (e.g. Ag-nanocoral) and a supply of electrons.

In this example, the method also includes a second electrochemical step, performed in a second electrolyzer module, for converting CO from the first electrochemical step and water into a multi-carbon alcohol (e.g. ethanol). The second electrochemical step includes exposing the CO and water to a second set of reaction conditions sufficient to form the multi-carbon alcohol. This second step is carried out by exposing the CO and water to a second catalyst (such as an oxide-derived nanocrystalline copper complex (OD-Cu) catalyst) and a supply of electrons. Other method steps may involve, for example, introducing a first reactant (e.g. $CO_2$) into the first electrolyzer module; transferring CO produced in the first module into the second module, and removing the final product from the second module. Further steps may include monitoring, detecting and/or characterizing the various species which are reacted and/or produced; prehydration of reactants to avoid evaporation of the electrolyte; as well as product quantification.

The production of a desired exemplary multi-carbon product Z from $CO_2$ in an exemplary 3-step reaction pathway can be described, for the purposes of illustration, as requiring the conversion of $CO_2$ to intermediate X in one step, conversion of intermediate X to intermediate Y in a second step, and conversion of intermediate Y in a third (and final) step to yield product Z, then for each step of the reaction, at least one suitable catalyst is selected or developed and suitable reaction conditions are identified to optimize production of at least one (usually only one) intermediate, as described above. With respect to a system for carrying out the reactions, the conversion of $CO_2$ to intermediate X is optimized and takes place in a first reaction module, the conversion of X to Y takes place in a second reaction module, and the conversion of Y to Z takes place in a third reaction module. Generally, the separate reactions are performed sequentially, i.e. $CO_2$ is first converted to X, then X is converted to Y, then Y is converted to Z. Since each reaction is generally performed in a separate reaction module, it is necessary to first introduce $CO_2$ into the first module, carry out the first reaction, and then transfer intermediate X (i.e. the product of the first reaction) from the first module to the second module; perform the second reaction and then transfer intermediate Y (i.e. the product of the second reaction) from the second module to the third module; perform the third reaction, and so on until the desired product had been produced, in this case "Z", which is produced by the third reaction in the third module. Z is then collected from the third module. This process is schematically illustrated in the high level flow chart depicted in FIG. 10, which shows module 1 connected to module 2 via conduit 4, and module 3 connected to module 2 via conduit 5. Conduits 4 and 5 represent means for transferring intermediate X from module 1 to module 2, and for transferring intermediate Y from module 2 to module 3, respectively. Also shown are inlet 6 through which $CO_2$ enters the system by moving directly into module 1, and outlet 7 through which product Z exits module 3.

Figure 11:
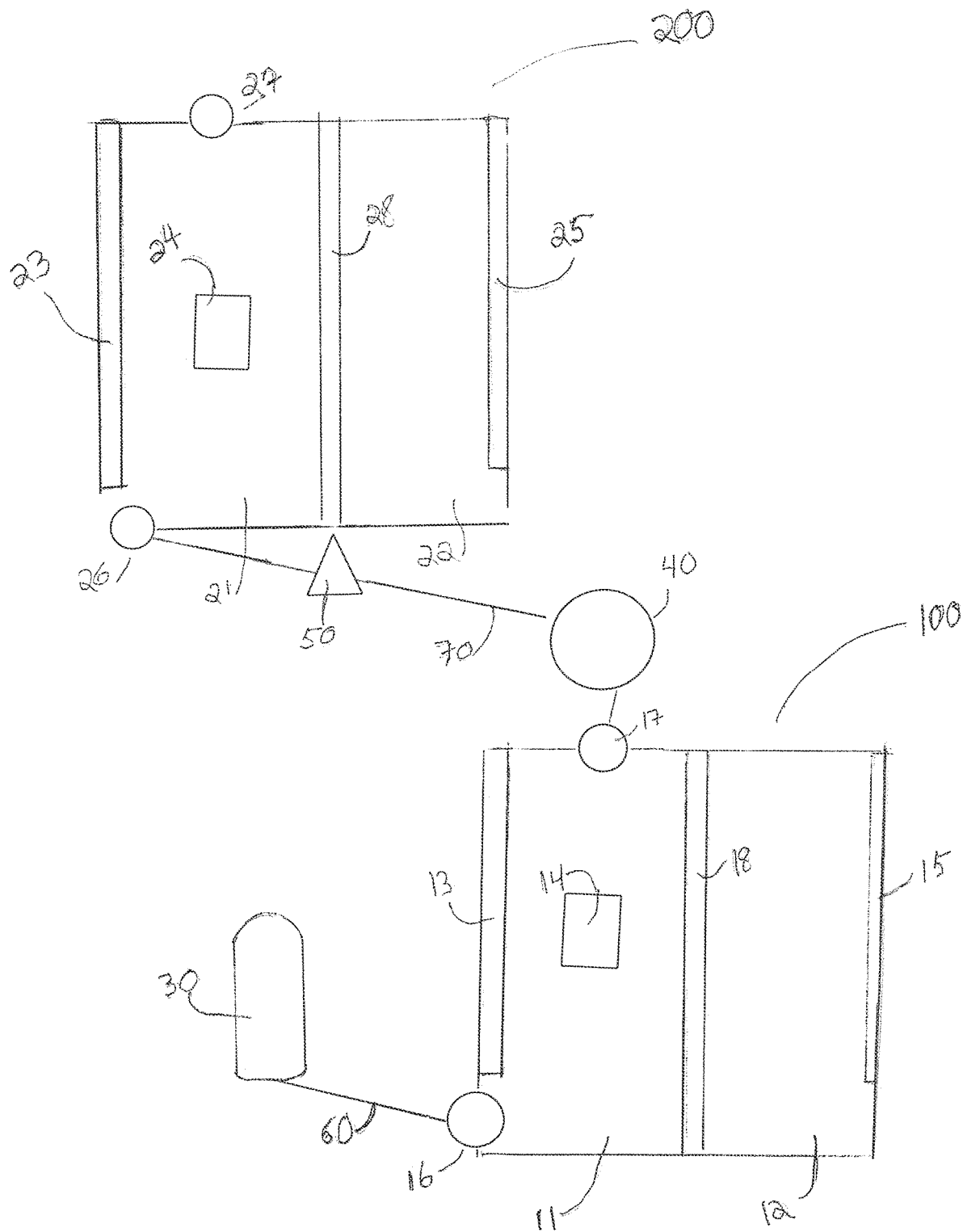
FIG. 11. High level schematic of a modular, sequential reaction system having 4 modules.

A more detailed schematic is shown in FIG. 11. In FIG. 11, a system for a reaction path with two reactions is shown. Shown are modules 100 and 200. Module 100 comprises compartments 11 and 12. Working electrode 13, reference electrode 14 and counter electrode 15 are shown, as are inlet 16, through which a first reactant is introduced into module 100 (coming from reactant source 30 and traveling through conduit 60), and outlet 17 through which a first intermediate leaves module 100. The first intermediate is transported from module 100 to module 200 via conduit 70, and enters module 200 via inlet 26. Module 200 contains working electrode 23, reference electrode 24 and counter electrode 25, and outlet 27 through which a final product leaves module 200. For a sustainable cascade system optimized for ethanol production, in some aspects the liquid catholyte of the second-stage electrolyzer is continually cycled through a separator (not shown) to isolate the $C_2H_5OH$ product before further reaction can occur.

Other optional components which are depicted include gas-liquid separator 40 and control valve 50.

Reactant source 30 may be or comprise one or more of a $CO_2$ absorption column, a $CO_2$ tank and/or a gas flow controller. Preferably, gaseous $CO_2$ is excluded from the electrolyzers using an upstream absorption column because the presence of small quantities of $CO_2$ in the second electrolyzer strongly impede the production of ethanol.

It is noted that the transfer of an intermediate product to the next reaction chamber may require recovery of the intermediate product, followed by the transfer; or the nature, amount and condition of the intermediate product may permit a direct and/or continuous, transfer to the next reaction chamber. Thus, conduits 60 and 70 are exemplary only and may be conduits for gases, liquids or solids, and/or may include additional components such as collection chambers for an intermediate that is collected prior to transport to the next module, various filters, valves, pumps, etc.

Figure 10:
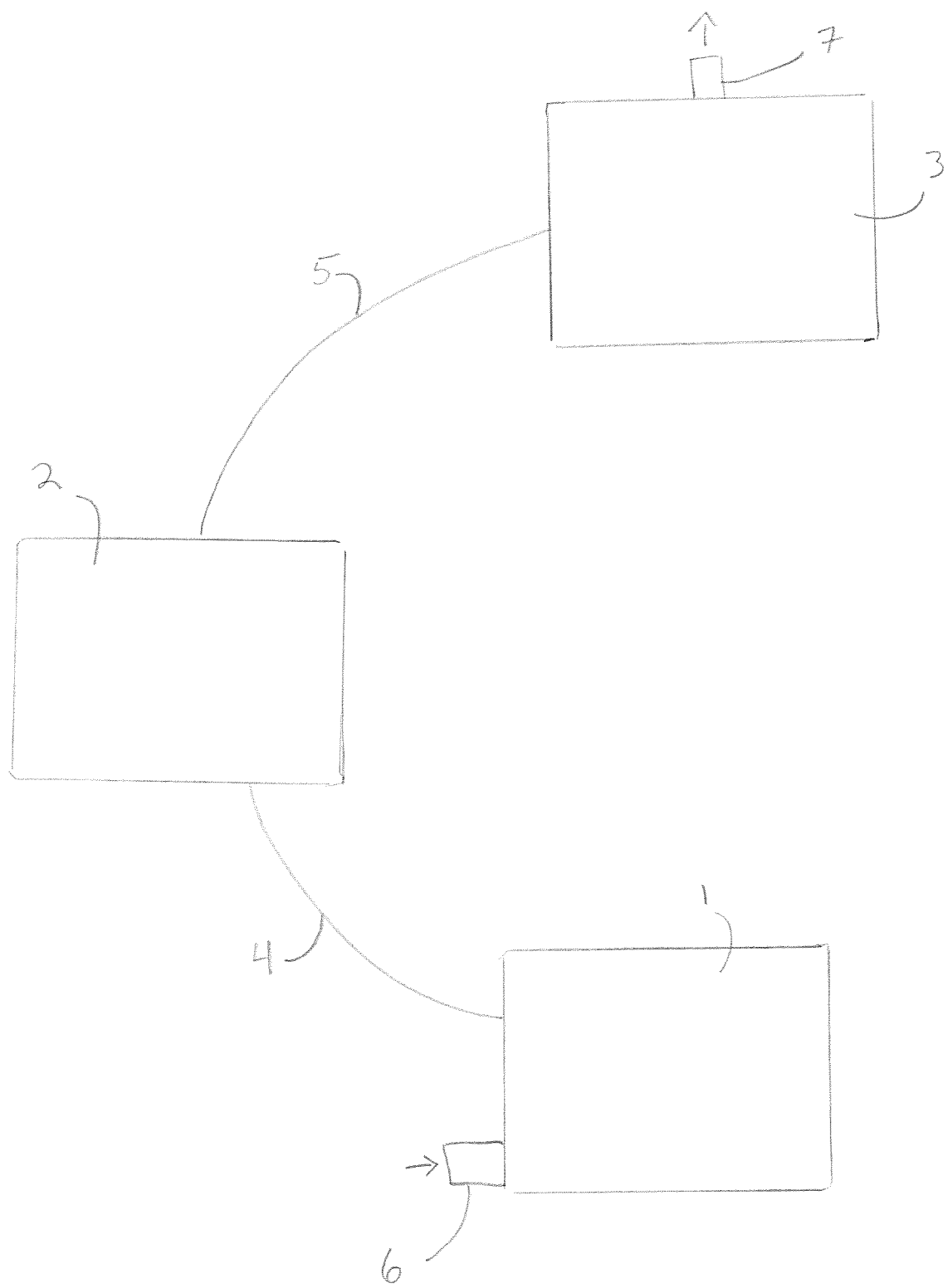
FIG. 10. High level schematic of a modular, sequential reaction system having 2 modules.

The systems depicted in FIGS. 10 and 11 depict the sequential reactions as linear. However, the reaction pathways may also branch, e.g. a particular combination of reactants and at least one catalyst under suitable reaction conditions may result in the formation of two or more useful products. In some aspects, both of the products are considered to be "intermediates" which are further reacted to form one or more desired end-products. The "further reactions" may be planned to occur via separate modular pathways, i.e. branched modular pathways are also contemplated Alternatively, in other aspects, one of the "intermediates formed in a reaction may be a desirable end-product, in which case that intermediate is collected, e.g. for further processing if necessary prior to use, while the other intermediate is separated and proceeds through further modular reactions.

In addition, while generally it is desired to produce a single intermediate in a single module, this is not always the case. For example, the energies and reaction conditions required for the conversion of intermediate X to intermediate Y and the conversion of intermediate Y to product Z may be similar, so that by using only one, or by using more than one, catalyst in the reaction chamber under the same optimized reaction conditions, Z can be efficiently produced in a single step. Alternatively, e.g. in a 5-step reaction, two of the steps are compatible and can be conducted in a single reaction chamber while the other 3 steps are performed separately.

While the present invention has been illustrated by the description of embodiments thereof and specific examples, and while the embodiments have been described in considerable detail, it is not intended to restrict or in any way limit the scope of the appended claims to such detail. Additional advantages and modifications will readily appear to those skilled in the art. Thus, the invention in its broader aspects is therefore not limited to the specific details, representative apparatus and methods and illustrative examples shown and described. Accordingly, departures may be made from such details without departing from the scope or spirit of applicant's general inventive concept.

It is to be understood that this invention is not limited to particular embodiments described herein above and below, and as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. at which the cell reaction takes place The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1. Heterogeneously Catalyzed Two-Step Cascade Electrochemical Reduction of $CO_2$ to Ethanol A cascade approach to preparation of a multi-carbon alcohol is an assembly line system with stepwise reactors with varying conditions tailored to optimize the kinetic rate and selectivity at each stage. The major advantage of an assembly line cascade is versatility and modularity. Each individual reaction can be operated with the optimal choice of catalyst, temperature, applied bias, etc., to maximize yield and minimize overpotential. This approach provides, on a systems level, greater product selectivity than could be achieved with a single heterogeneous catalyst. From an energy efficiency standpoint, the cascade reaction requires the same number of total electron-transfer steps as the single complex reaction and produces a similar amount of product species on a faradaic current basis. The cascade electrolyzers are not in electrical series, so the overpotentials from each step in the reaction sequence are not additive but rather averaged across the total system weighted by the charge passed at each potential, and each individual reaction is designed for maximum kinetic rates at high product yields. This advantage is a critical distinction between a sequential cascade reactor design and a one-pot cascade, in which all the complementary catalysts are forced to operate at the same conditions at the same applied bias. This novel systems approach enables better design of electrochemical processes, e.g. for turning waste $CO_2$ into a variety of useful products at better energy efficiency and selectivity than previously achievable.

In this example, the viability of multistage cascade electrolysis to produce $C_2H_5OH$ from $CO_2$ was demonstrated. The overall cathode half-reaction for ethanol formation is

Ethanol production was pursued by splitting this reaction into two distinct electrochemical steps. CO was targeted as the stable intermediate product from the first stage

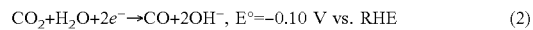

Among numerous electrocatalytic systems which have shown high selectivity for CO formation, etched Ag nanocoral (Ag—NC) films have achieved >95% faradaic efficiency at only −0.5 V vs. RHE with promising stability. Furthermore, oxide-derived nanocrystalline Cu (OD-Cu) catalysts have reduced CO to $C_2H_5OH$ at ~43% faradaic efficiency at only −0.3 V vs. RHE following the reaction:

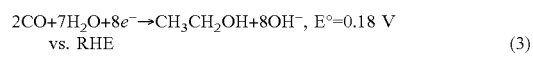

These catalytic systems were leveraged to demonstrate the cascade approach as a rational strategy for targeting high faradaic efficiency of a complex product at a low overall overpotential.

EXPERIMENTAL

A. Electrode Preparation. Ag—NC foil was used as the $CO_2RR$ catalyst for the first-stage electrolysis cell, along with an OD-Cu foil electrode for the second-stage electrolysis cell. The Ag—NC was prepared from a Ag foil (99.999% pure, Alfa Aesar) by first producing a AgCl surface by electrochemical oxidation at 0.3 V vs. Ag/AgCl in 0.1 M KCl electrolyte for 12 h. Subsequently, the foil was reduced to nanocoral structure by applying a potential of −1.2 V vs. Ag/AgCl in the same electrolyte for 30 min.

The OD-Cu electrode was fabricated from a Cu foil (99.98% pure, Alfa Aesar) which was cleaned with a 1 M HCl soak for 2 minutes, then rinsed with isopropyl alcohol and water. The Cu foil was then dried with $N_2$ gas (99.99% pure) and then heated at 500° C. for 1 h under atmospheric air. Following thermal oxidation, the foil was cooled gradually to room temperature over ~1 h to prevent delamination of the oxide layer. The thermally oxidized Cu foil was electrochemically reduced at −0.6 V vs. RHE in 0.1 M KOH solution for 45 min. After the reduction process, fresh electrolyte was added to the cell prior to CO reduction. B. Cascade Electrolyzer Design. The generalized layout of the cascade system is depicted in the schematic of FIG. 1. $CO_2$ (99.99%, Specialty Gases) was flowed at 20 sccm with a mass flow controller through a custom absorption column filled with 0.1 M $KHCO_3$ in 18 MΩ-cm water in a random packing of 1 mm diameter glass beads. The liquid electrolyte was cycled with a peristaltic pump through the column and the cathode section of the first electrolyzer at a rate of 80 mL $min^{-1}$. The flow rates were chosen to provide near saturation of $CO_2$ in the electrolyte at the column outlet and to avoid transferring gaseous $CO_2$ bubbles to the first-stage electrolyzer. From the cathode (Ag—NC) of the first electrolysis cell, the electrolyte flowed into a separate chamber for an extended residence time, permitting the effective separation of product CO and $H_2$ bubbles from the liquid, with the electrolyte recycled back to the inlet of the $CO_2$ absorption column. The gaseous product output from the separation chamber of the first-stage electrolyzer was directed to the second-stage electrolyzer through a porous glass frit bubbler positioned at the bottom of the 0.1 M KOH catholyte to promote gas dissolution and mass transfer to the OD-Cu cathode. There was no pump in between the electrolyzer stages, with the evolution of gases in the first stage being the driver for gaseous flow.

C. Electrochemical Measurements. The first-stage electrolyzer was a custom-designed two-compartment polycarbonate cell with a large Ag—NC working electrode geometric surface area (~11 $cm_2$), a Pt mesh counter electrode, and a Ag/AgCl (3 M KCl) reference electrode. An anion exchange membrane (Selemion AMV) separated the Ag—NC cathode and reference from the Pt anode with 0.1 M $KHCO_3$ (pH 6.8) electrolyte in both chambers. The second-stage electrolysis cell was a similar two-compartment polycarbonate cell designed to maximize catalyst area relative to the electrolyte volume, enabling higher sensitivity for liquid product detection. An OD-Cu foil working electrode of ~5 $cm^2$ geometric surface area was used along with a Ag/AgCl (3 M KCl) reference electrode in the cathode compartment and a Pt mesh counter electrode in the anode compartment. The same Selemion anion exchange material was used as a membrane but with 0.1 M KOH electrolyte. Electrochemical measurements were performed with either one (for an individual electrolyzer) or two (for the two-step cascade) Biologic SP-200 potentiostats. Potentiostatic electrochemical impedance spectroscopy measurements were performed before every experiment to determine the uncompensated cell resistance, $R_u$, and the potentiostat subsequently compensated for 85% of $R_u$ in each cell during electrolysis. Potentials were converted to the reversible hydrogen electrode (RHE) utilizing the Nernst equation according to $V_{RHE}=V_{Ag/AgCl}+ 0.210+0.059*pH_{soln}$.

D. Product Quantification. Gaseous products were measured by gas chromatography (GC, SRI 8610) and liquid products were measured with nuclear magnetic resonance (NMR, Bruker 400 MHz) spectroscopy. Both the liquid and gas phase product concentrations were determined using calibrations from known standards. The gas phase products were injected into the GC via automatic valve injection (1 mL sample) with a thermal conductivity detector (TCD) and a flame ionization detector (FID). Nitrogen (99.99% Specialty Gases) was utilized as a carrier gas to permit accurate hydrogen quantification. For potentiostatic measurements, an injection to the GC was made after 5 min and then after each subsequent 30 min. Liquid samples for $^1H$ NMR spectroscopy were taken periodically throughout the experiment and at the end of each experiment. Samples were prepared by mixing $D_2O$ and electrolyte aliquots in a 1:1 volume ratio. Dimethyl sulfoxide (DMSO) was added at a known low concentration for internal calibration.

Faradaic efficiency was calculated for the potentiostatic measurements by determining the charge required to produce the measured product concentration and dividing by the total charge passed during the time the sample underwent electrolysis. For the two-stage cascade experiments, the faradaic efficiency of ethanol was defined from $CO_2$ to $C_2H_5OH$ across the entire system, as the charge required to produce the measured $C_2H_5OH$ from $CO_2$ (12 mol $e^-$ required per mol $C_2H_5OH$) divided by the sum of the charge passed in both electrolysis cells.

Results and Discussion

Figures 2A, 2B:
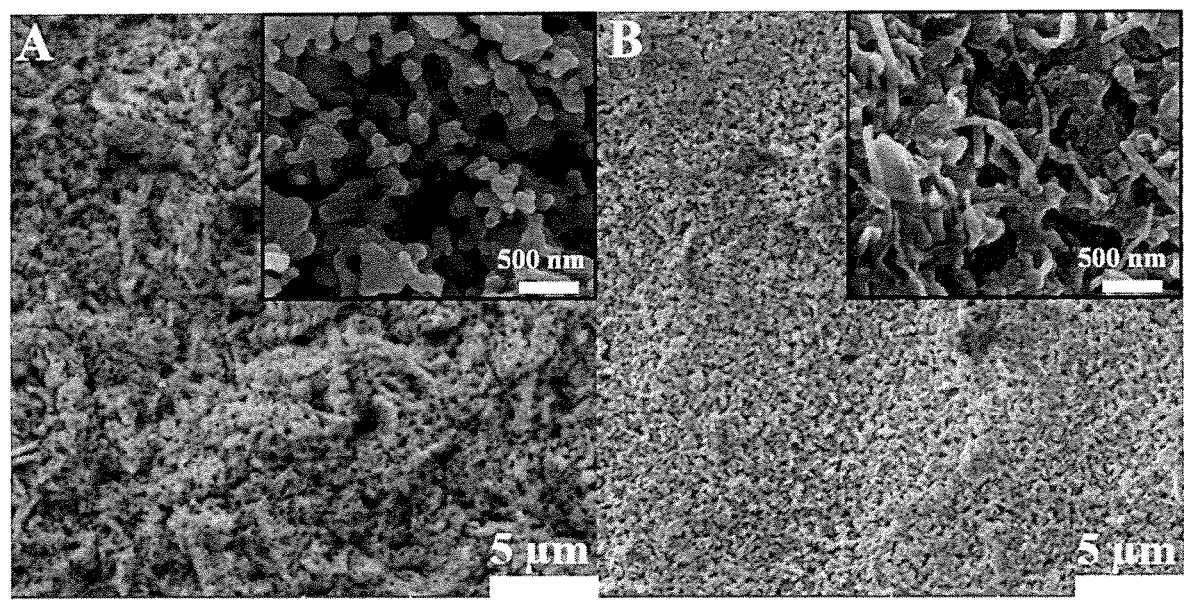
FIGS. 2A and B. SEM images of (A) the Ag—NC catalyst of the first-stage electrolyzer and (B) OD-Cu of the second-stage electrolyzer.
Figures 3A, 3B:
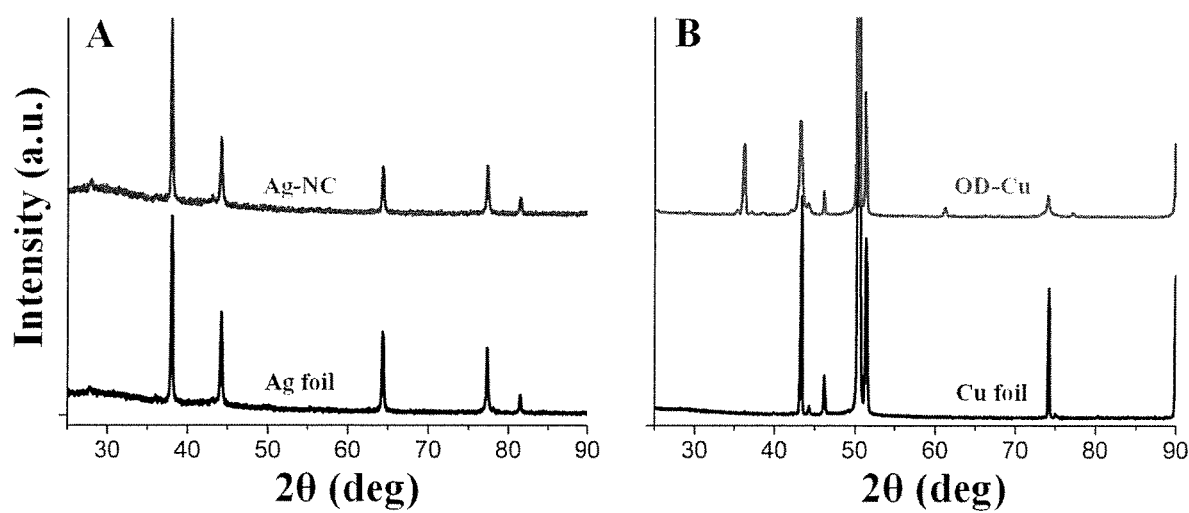
FIGS. 3A and B. XRD data for (A) Ag—NC catalyst (top) compared to unaltered polycrystalline Ag foil (bottom) and (B) OD-Cu (top) compared to unaltered polycrystalline Cu foil (bottom).

A. Individual Electrolyzer Performance. The two electrolysis reactors were first characterized independently to establish their expected performance characteristics and to identify the optimal operating conditions for their combination in a cascade system. FIGS. 2A and B shows the surface of each electrocatalyst, which displayed the expected morphology of the nanoporous coral-like structure for the Ag—NC catalyst and the rough nanoparticulate surface of the OD-Cu. FIG. 3 shows the faradaic efficiency of the reaction products for each electrolyzer as a function of applied potential, as well as the product distribution vs. time for the applied bias which resulted in the maximum faradaic efficiency for the desired product (i.e., CO for the first electrolyzer, $C_2H_5OH$ for the second electrolyzer). Using the upstream $CO_2$ absorption column to feed $CO_2$-saturated 0.1 M $KHCO_3$ to the Ag—NC electrocatalyst, a peak faradaic efficiency of 80% was achieved for CO at −0.6 V vs. RHE (FIG. 3A). The CO production performance at this potential was quite steady for $CO_2$ electroreduction, dropping only ~2% over >1 h (FIG. 3C). The observed peak CO faradaic efficiency was lower than the 95% reported previously, which was attributed to supplying the $CO_2$ feedstock exclusively as a dissolved gas without active bubbling in the catholyte in contrast to previous work. In the absence of active reactant gas bubbling across the electrocatalyst surface, $CO_2$ mass transport limitations arise which inhibit CO formation and permit greater hydrogen evolution instead. Despite the slight reduction in CO faradaic efficiency, the $CO_2$ absorption column was employed to minimize the concentration of $CO_2$ entering the outlet gas stream from the Ag—NC cathode chamber. The cathode outlet gas flow rate was measured to be 1.2 sccm, which was due to production of $CO/H_2$ gas. No $CO_2$ was detected in this outlet flow by GC. To independently test the second electrolyzer, pure CO (>99.9%) was bubbled at 20 sccm below the OD-Cu electrocatalyst in the 0.1 M KOH catholyte. A peak faradaic efficiency for ethanol of 40% occurred at −0.3 V vs. RHE, with 12% for acetic acid and ~1% ethylene (FIG. 3B). Monitoring performance at this operating potential vs. time, marginally higher $CO_2$ reduction values and lower hydrogen was observed (some trace ethane was measured over time as well, FIG. 3D).

Figure 4A:
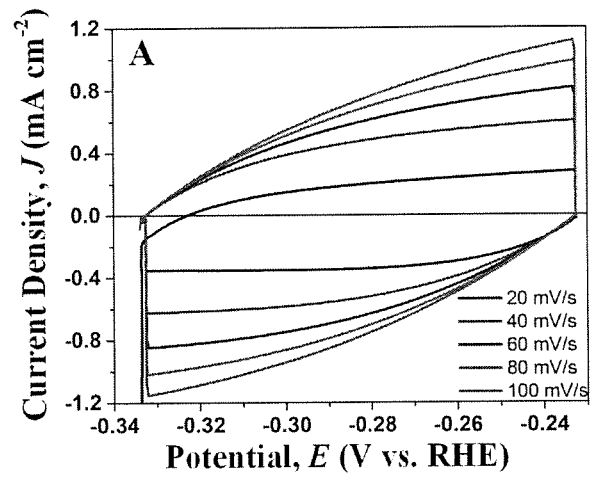
FIG. 4A-C. Double layer capacitance measurements for the determination of roughness factor based on electrochemically active surface area. Scan-rate dependent behavior for (A) Ag—NC and (B) OD-Cu catalysts, and (C) cathodic and anodic charging currents as a function of scan rate for both catalysts and a polished Ag foil reference.
Figure 4B:
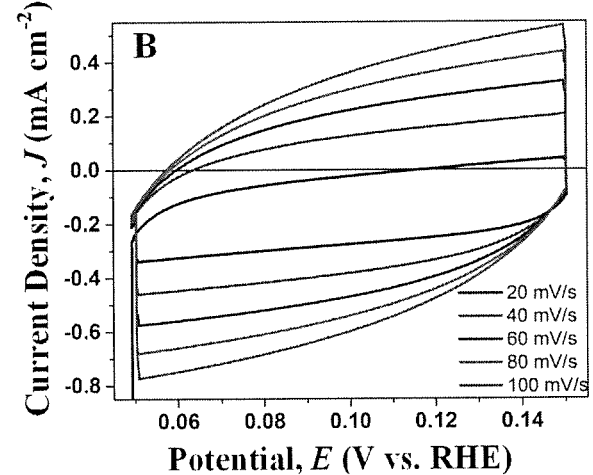
Figure 4C:
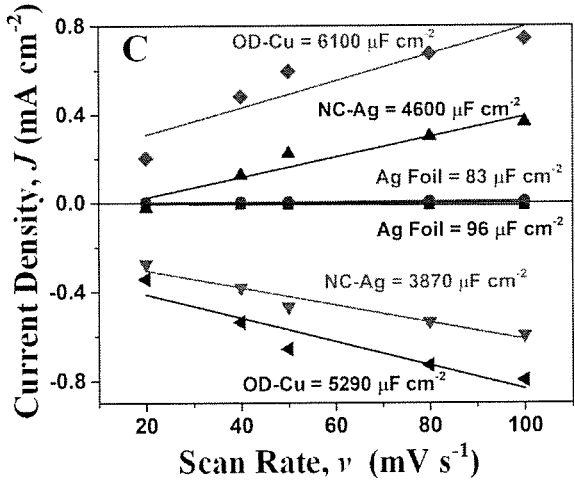

B. Cascade Electrolysis System Performance. After establishing the first- and second-stage electrolyzer operating potentials for optimal faradaic efficiency, the full cascade system was assembled and measured following the layout in FIG. 1. $CO_2$-saturated electrolyte was circulated through the cathode of the first electrolyzer, and the product $CO/H_2$ gases were bubbled into the second electrolyzer under the pressure created by their evolution during the electrochemical reaction. Separate potentiostats held the independent operating potentials for each electrolyzer and monitored the current density throughout the reaction. FIG. 4 shows the current density vs. potential behavior of the first-stage (Ag—NC, 0.1 M $KHCO_3$) and second-stage (OD-Cu, 0.1 M KOH) electrolyzers as well as the current density vs. time for the experiment. After an initial drop in the current density from the OD-Cu, the two electrolyzers at these operating potentials reached steady state current densities of comparable magnitude (~1-2 mA cm$^{-2}$). The higher initial current density from the OD-Cu may be attributable to the reduction of a surface oxide which remained despite the catalyst pretreatment.

Table 1 shows the system parameters and product faradaic efficiency measured for the two-step cascade electrolysis. The output of the first cell was difficult to sample without interrupting the behavior of the cascade, so the CO faradaic efficiency in the output was assumed equal to that measured in the independently operated Ag—NC electrolyzer (FIG. 3). A liquid aliquot of the second electrolyzer catholyte was collected after 40 min of operation and analyzed by NMR to determine the ethanol concentration. Based on the charge passed in the second cell only, the average $C_2H_5OH$ faradaic efficiency was 28.4%. This result is less than the 42% measured for the individual OD-Cu electrolyzer with pure CO feedstock (FIG. 3), which was attributed to the ~20% $H_2$ content in the gas stream to the second cell of the cascade, as examined further below. The average total faradaic efficiency for $C_2H_5OH$ was 11.0% based on the total charge passed between both electrolyzers in the cascade.

TABLE 1

Key parameters for the $CO_2$ to ethanol two-step cascade electrolysis

| First Electrolyzer | | | |
| --- | --- | --- | --- |
| Catalyst | Electrolyte | Operating Potential | CO FE (%)[a] |
| Ag-NC | 0.1M $KHCO_3$ | −0.6 V vs RHE | 80 |

| Second Electrolyzer | | | |
| --- | --- | --- | --- |
| Catalyst | Electrolyte | Operating Potential | $COH_5OH$ FE (%)[b] |
| OD-Cu | 0.1M KOH | −0.3 V vs RHE | 28.4 |

| Total Cascade Electrolyzer System | | |
| --- | --- | --- |
| CO to $C_2H_5OH$ Conversion (%) | Average Potential[c] | $COH_5OH$ FE (%)[d] |
| 6.4 | −0.52 V vs RHE | 11.0 |

[a]First-stage electrolyzer CO faradaic efficiency estimated from values determined at the same conditions for the independently measured Ag-NC system.
[b]Determined from ethanol content measured in the second electrolyzer after 40 min of cascade system operation, based on the charge passed at the OD-Cu only.
[c]Average applied potential across the two electrolyzers of the cascade, weighted by the charge passed in each electrolyzer.
[d]Determined from ethanol content measured in the second electrolyzer after 40 min of cascade system operation, based on the total charge passed between both electrolyzers.

The cascade electrolysis faradaic efficiency for $CO_2RR$ to ethanol of 11.0% is not as high as has been reported for some other systems at high applied potential (Table 2), but it compares favorably to state-of-the-art catalysts at modest cathodic potential (~−0.5 V vs. RHE). Comparison of the overpotential for ethanol formation between a single electrolysis step and the cascade system is complicated by having two different operating potentials in the two-step electrolysis. Although the two electrolyzers are connected in series for the chemical flow, they are independent electrical loads. Rather than additive voltages as would occur in electrical series, the overall cascade system overpotential for $CO_2$ conversion to $C_2H_5OH$ is a weighted average of the two electrolyzer overpotentials. Ideally, the net potential in the cascade system for the 12 electrons needed to convert 2 $CO_2$ molecules to $C_2H_5OH$ (Eqn. 1) is the weighted average of the applied potential in the first stage for the 4 electrons needed to make 2 CO molecules (Eqn. 2) and the applied potential in the second stage for the 8 electrons needed to convert the 2 CO molecules to $C_2H_5OH$ (Eqn. 3). For the reported cascade system operating potentials, this ideal net potential is −0.4 V vs. RHE, corresponding to a cathodic overpotential of ~490 mV for ethanol production (Eqn. 1). Practically, for a system with byproducts and less than perfect conversion of the intermediate product (i.e., CO), the average system applied potential should be weighted by the total charge passed in each electrolysis step. For the reported two-step cascade, this average system operating potential is −0.52 V vs. RHE, corresponding to a cathodic overpotential of ~610 mV for ethanol production.

TABLE 2

Literature reports of the performance of electroreduction of $CO_2$ to ethanol.

| Catalyst | Electrolyte | Potential | $C_2H_5OH$ FE (%) |
| --- | --- | --- | --- |
| polycrystalline Cu | 0.1M $KHCO_3$ | −1.05 V vs. RHE | 9.8 |
| Cu (100) | 0.1M $KHCO_3$ | −1.00 V vs. RHE | 9.7 |
| Cu (110) | 0.1M $KHCO_3$ | −1.18 V vs. RHE | 10.5 |
| Cu (111) | 0.1M $KHCO_3$ | −1.15 V vs. RHE | 2.6 |
| Cu (310) | 0.1M $KHCO_3$ | −1.02 V vs. RHE | 29.9 |
| $Cu_2O$ microparticles on Cu | 0.1M $KHCO_3$ | −0.99 V vs. RHE | 16.4 |
| OD-Cu particles | 0.1M $KHCO_3$ | −0.98 V vs. RHE | 11.8 |
| $Cu_4Zn$ fil | 0.1M $KHCO_3$ | −1.05 V vs. RHE | 29.1 |
| Cu nanoparticles on GDE[a] | 1M KOH | −0.80 V vs. RHE | 17.0 |
| CuDAT-wire[b] | 1M KOH | −0.60 V vs. RHE | 25.0 |
| Ag-NC/OD-Cu Cascade[c] | 0.1M $KHCO_3$/ 0.1 KOH[c] | −0.52 V vs. RHE[c] | 11.0[c] |

[a]Gas diffusion electrode (GDE)
[b]3,5-diamino-1,2,4-triazole (DAT)
[c]The cascade system of this work, with Ag nanocoral (Ag-NC) in 0.1M $KHCO_3$ in the first stage and oxide-derived Cu(OD-Cu) in 0.1M KOH in the second stage. The average applied potential of the system as weighted by the charge passed in each stage, and the faradaic efficiency based on the charge passed in both stages.

Figure 5A:
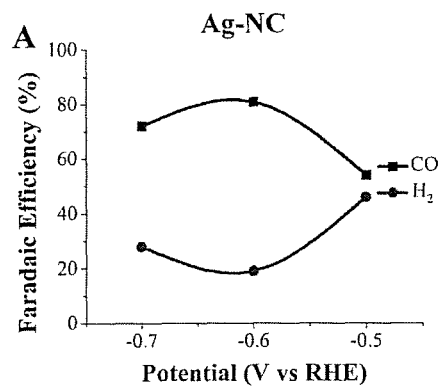
FIG. 5A-D. Individual electrolyzer performance. Peak product faradaic efficiency for (A) the first electrolyzer with Ag—NC catalyst in 0.1 M $KHCO_3$ saturated with pure $CO_2$ and (B) the second electrolyzer with OD-Cu catalyst in 0.1 M KOH bubbled with pure CO. (C) Product faradaic efficiencies vs. time for the electrolyzer from (A) held at −0.6 V vs. RHE. (D) Product faradaic efficiencies vs. time for the electrolyzer from (B) held at −0.3 V vs. RHE. Liquid products were sampled and measured at the end of the experiment.
Figure 5B:
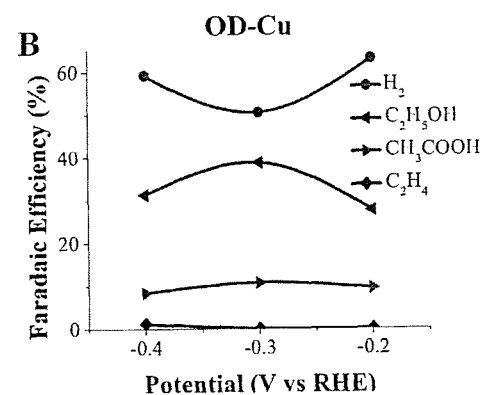
Figure 5C:
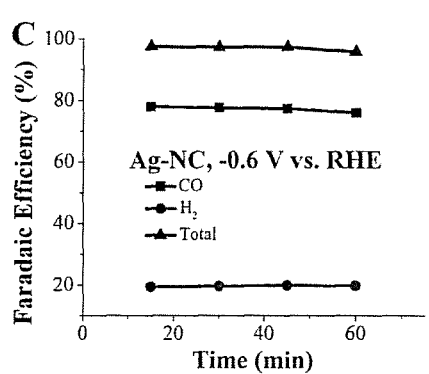
Figure 5D:
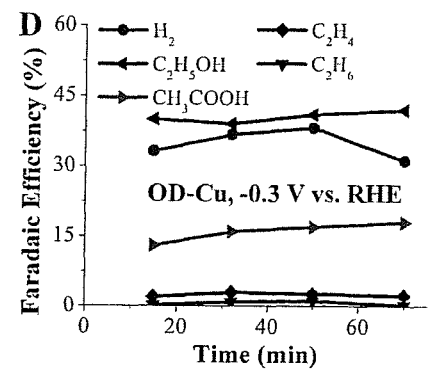
Figure 6:
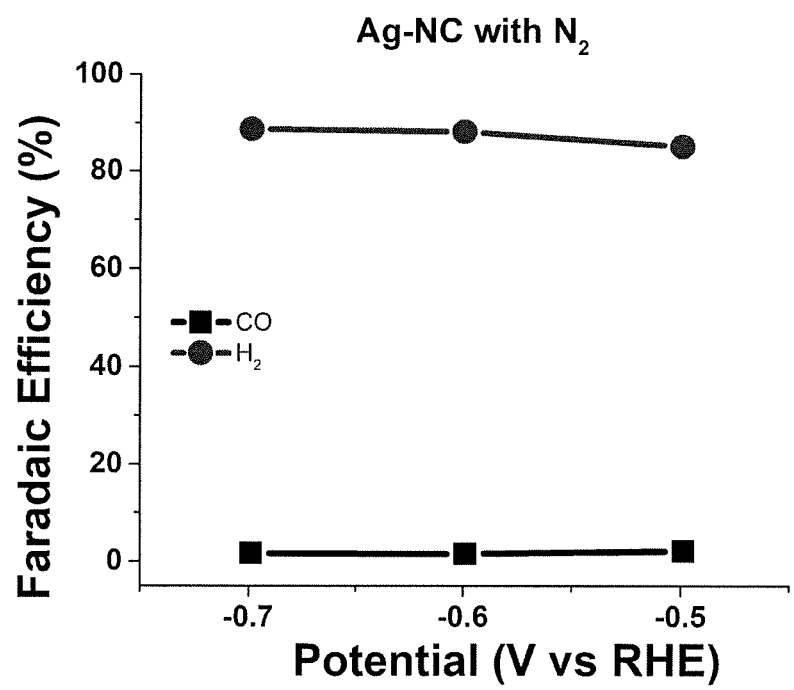
FIG. 6. Faradaic efficiency vs. potential for Ag—NC catalyst in 0.1 M $KHCO_3$ saturated with $N_2$ in the absence of $CO_2$.
Figure 9:
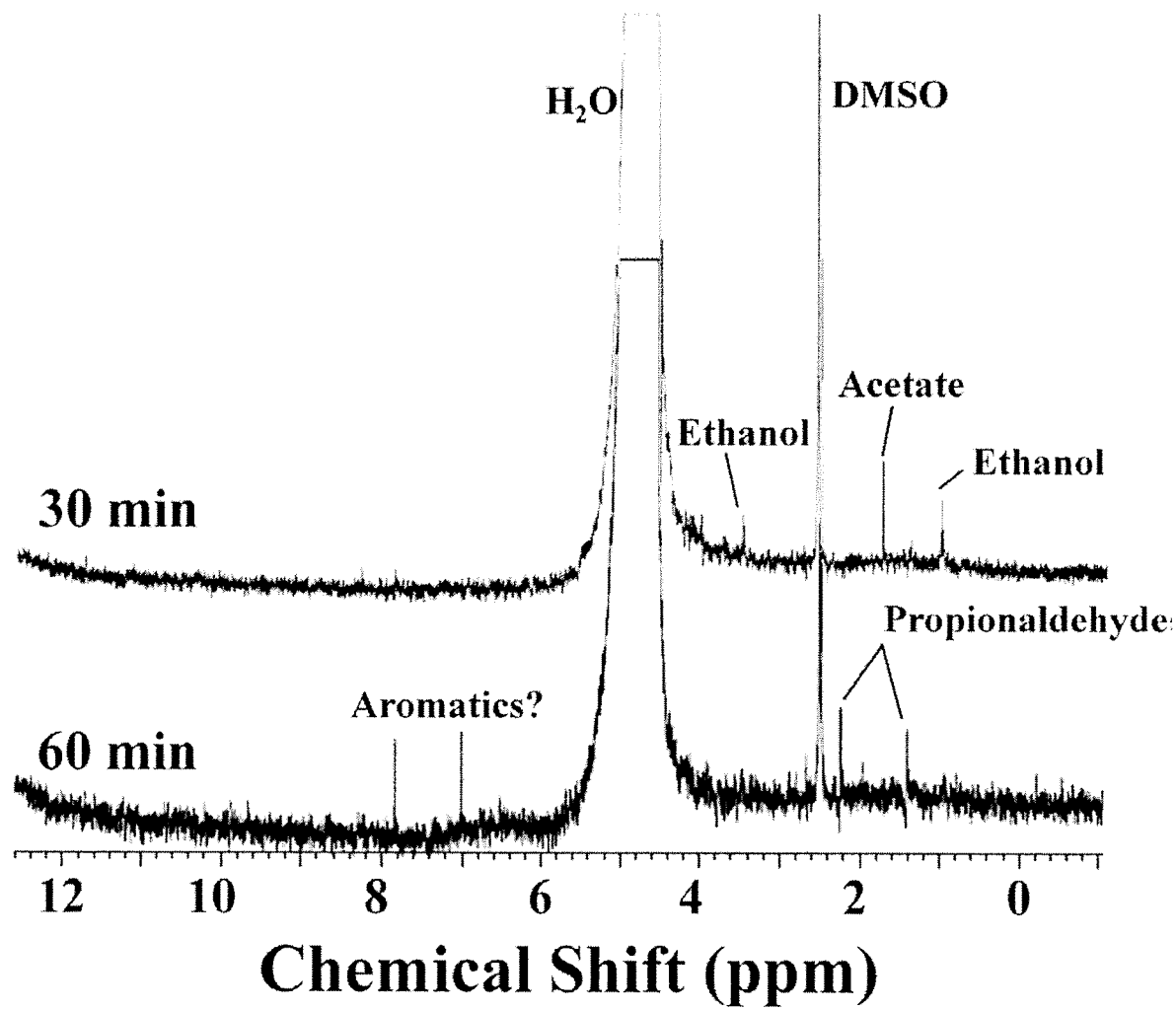
FIG. 9. NMR spectra for liquid products of the cascade electrolysis after operation for 30 min (green) and for 60 min (black). DMSO was used as an internal standard.

While a high selectivity to $C_2H_5OH$ in the second-stage electrolyzer with OD-Cu was confirmed with a pure CO feed, the presence of CO, and/or $H_2$ was expected to introduce competing reactions which could reduce the faradaic efficiency for ethanol formation. The $CO_2$ absorption column was thus incorporated into the cascade system upstream of the first-stage electrolyzer to prevent excess non-dissolved $CO_2$ from carrying over to the second reactor. The effect of $CO_2/H_2$ in the feed to the second cell was simulated using a controlled gas mixture in an individual measurement on the OD-Cu system (FIG. 5). Using a 4:1 CO:$H_2$ (no $CO_2$) gas flow in accordance with the expected product from the first stage, the OD-Cu cathode displayed 28% faradaic efficiency for $C_2H_5OH$ after 40 min, with significantly reduced acetate production compared to a pure CO feed. Furthermore, dilution of this mixed flow with 5% $CO_2$ by volume decreased the ethanol faradaic efficiency to 5%, which dropped to <3% at 10% $CO_2$, and acetate was no longer detected as a side product. Thus, exclusion of $CO_2$ from the second cell catholyte was deemed critical to performance. Furthermore, with the 4:1 CO:H, (no $CO_2$) gas flow composition, the faradaic efficiency for ethanol was observed to be time-dependent. As shown in FIG. 5B, the cumulative $C_2H_5OH$ faradaic efficiency decreased with time beyond 30 min.

After 30 min of cascade system operation, NMR peaks for ethanol were clearly evident at a chemical shift of 1.0 and 3.5 ppm. After 1 h, the ethanol signal was largely replaced with new peaks at 1.4, 2.2, 7.0 and 7.8 ppm. The lower two peaks are consistent with the presence of propionaldehyde, a three-carbon ($C_3$) species that has previously been observed in small amounts as a product of $CO_2$ reduction on copper cathodes. In the absence of nitrogen bonding, peaks in the 7-8 ppm range for $^1H$ NMR are generally attributed to aromatic compounds. It can thus be inferred that in the presence of $CO/H_2$, at reductive potentials in the second electrolyzer, the $C_2H_5OH$ was further reduced to $C_{3+}$ species.

SUMMARY

In this work, the multistep proton-coupled electron-transfer reaction for the conversion of $CO_2$ to $C_2H_5OH$ was strategically divided into two independently optimized steps in a sequential cascade reaction using heterogeneous electrocatalysts to convert $CO_2$ to CO and CO to $C_2H_5OH$ within a single integrated electrochemical system. With a stable intermediate species between reactors (e.g., CO in this work), each electrochemical conversion step was optimized for maximum faradaic efficiency and minimum overpotential by independently controlling the operating parameters. The exclusion of $CO_2$ reactant from the second-stage electrolyzer was observed to be critical for maintaining appreciable ethanol selectivity. The cascade system produced $C_2H_5OH$ at an overall faradaic efficiency of 11.0% at an average applied potential of −0.52 V vs. RHE, making it highly competitive with known single-step electrocatalysts for ethanol production from $CO_2$. The primary advantage of this multistage cascade electrolysis approach is its versatility and modularity. The two electrolyzers employed in the cascade system of this work operated simultaneously with different applied biases, electrolytes, and electrocatalysts. The cascade approach thus is a viable generic strategy to achieve higher selectivity for the electrochemical synthesis of more complex products.

Example 2. Projected Cascade System Performance Calculations

A. Perfect CO Conversion with Present System Parameters.

If a recycle stream or modified reactor design allowed complete conversion of the CO intermediate while maintaining the other measured system performance characteristics (Table 1, 80% faradaic efficiency for CO at −0.6 V vs. RHE in electrolyzer 1, 28.4% faradaic efficiency for $C_2H_5OH$ at −0.3 V vs. RHE in electrolyzer 2 with 7.4% faradaic efficiency for acetate, with the balance towards $H_2$), the following calculation is made:

Assuming a basis of 1 C of charge passed in the first electrolyzer:

$$(1\ C)\left(\frac{mol\ e^-}{96485\ C}\right)(0.08)\left(\frac{1\ mol\ CO}{2\ mol\ e^-}\right) = 4.15 \times 10^{-6}\ mol\ CO$$

The moles of electrons passed in the second electrolyzer to convert all the CO:

$$\frac{4.15 \times 10^{-6}\ mol\ CO}{\left(\frac{2\ mol\ CO}{mol\ C_2H_5OH}\right)\left(8\frac{0.284}{\frac{mol\ e^-}{mol\ C_2H_5OH}}\right) + \left(\frac{2\ mol\ CO}{mol\ CH_3COOH}\right)\left(4\frac{0.074}{\frac{mol\ e^-}{mol\ CH_3COOH}}\right)} = 3.84 \times 10^{-5}\ mol\ e^-$$

Charge passed in the second electrolyzer:

$$(3.84 \times 10^{-5}\ mol\ e^-)\left(\frac{96485\ C}{mol\ e^-}\right) = 3.71\ C$$

Moles of ethanol produced:

$$(3.84 \times 10^{-5}\ mol\ e^-)(0.284)\left(\frac{mol\ C_2H_5OH}{8\ mol\ e^-}\right) = 1.36 \times 10^{-6}\ mol\ C_2H_5OH$$

Faradaic efficiency for ethanol across the entire cascade system:

$$\frac{(1.36 \times 10^{-6}\ mol\ C_2H_5OH)\left(\frac{12\ mol\ e^-}{mol\ C_2H_5\ OH}\right)\left(\frac{96485\ C}{mol\ e^-}\right)}{(1\ C) + (3.71\ C)} = 0.334 = 33.4\%$$

Average applied potential for the entire cascade system:

$$\frac{(-0.6\ V)(1\ C) + (-0.3\ V)(3.71\ C)}{(1\ C) + (3.71\ C)} = -0.36\ V$$

B. Perfect CO Conversion with State-of-the-Art System Parameters.

If state-of-the-art $CO_2$-to-CO (98% faradaic efficiency with Ag in ionic liquid at ~−0.25 V vs. RHE) and CO-to-$C_2H_5OH$ (42% faradaic efficiency for ethanol with 11% faradaic efficiency for acetate, with the balance towards $H_2$ with OD-Cu in 0.1 M KOH at −0.3 V vs. RHE) electrochemical conversion performance characteristics were combined with 100% CO conversion in a perfect recycle stream, the following calculation is made:

Assuming a basis of 1 C of charge passed in the first electrolyzer:

$$(1\ C)\left(\frac{mol\ e^-}{96485\ C}\right)(0.98)\left(\frac{1\ mol\ CO}{2\ mol\ e^-}\right) = 5.08 \times 10^{-6}\ mol\ CO$$

The moles of electrons passed in the second electrolyzer to convert all the CO:

$$\frac{5.08 \times 10^{-6}\ mol\ CO}{\left(\frac{2\ mol\ CO}{mol\ C_2H_5\ OH}\right)\left(8\frac{0.42}{\frac{mol\ e^-}{mol\ C_2H_5OH}}\right) + \left(\frac{2\ mol\ CO}{mol\ CH_3COOH}\right)\left(4\frac{0.11}{\frac{mol\ e^-}{mol\ CH_3COOH}}\right)} = 3.18 \times 10^{-5}\ mol\ e^-$$

Charge passed in the second electrolyzer:

$$(3.18 \times 10^{-5} \text{ mol } e^-)\left(\frac{96485 \text{ C}}{\text{mol } e^-}\right) = 3.07$$

Moles of ethanol produced:

$$(3.18 \times 10^{-5} \text{ mol } e^-)(0.42)\left(\frac{\text{mol C}_2\text{H}_5\text{OH}}{8 \text{ mol } e^-}\right) = 1.67 \times 10^{-6} \text{ mol C}_2\text{H}_5\text{OH}$$

Faradaic efficiency for ethanol across the entire cascade system:

$$\frac{(1.67 \times 10^{-6} \text{ mol C}_2\text{H}_5\text{OH})\left(\frac{12 \text{ mol } e^-}{\text{mol C}_2\text{H}_5\text{OH}}\right)\left(\frac{96485 \text{ C}}{\text{mol } e^-}\right)}{(1 \text{ C}) + (3.07 \text{ C})} = 0.465 = 47.5\%$$

Average applied potential for the entire cascade system:

$$\frac{(-0.25 \text{ V})(1 \text{ C}) + (-0.3 \text{ V})(3.07 \text{ C})}{(1 \text{ C}) + (3.07 \text{ C})} = -0.29 \text{ V}$$

B. Perfect CO Conversion with State-of-the-Art System Parameters.

If state-of-the-art $CO_2$-to-CO (98% faradaic efficiency with Ag in ionic liquid at ~−0.25 V vs. RHE) and CO-to-$C_2H_5OH$ (42% faradaic efficiency for ethanol with 11% faradaic efficiency for acetate, with the balance towards $H_2$ with OD-Cu in 0.1 M KOH at −0.3 V vs. RHE) electrochemical conversion performance characteristics were combined with 100% CO conversion in a perfect recycle stream, the following calculation is made:

Assuming a basis of 1 C of charge passed in the first electrolyzer:

$$(1 \text{ C})\left(\frac{\text{mol } e^-}{96485 \text{ C}}\right)(0.98)\left(\frac{1 \text{ mol CO}}{2 \text{ mol } e^-}\right) = 5.08 \times 10^{-6} \text{ mol CO}$$

The moles of electrons passed in the second electrolyzer to convert all the CO:

$$\frac{5.08 \times 10^{-6} \text{ mol CO}}{\left(\frac{2 \text{ mol CO}}{\text{mol C}_2\text{H}_5\text{ OH}}\right)\left(8\frac{\frac{0.42}{\text{mol } e^-}}{\text{mol C}_2\text{H}_5\text{OH}}\right) + \left(\frac{2 \text{ mol CO}}{\text{mol CH}_3\text{COOH}}\right)\left(4\frac{\frac{0.11}{\text{mol } e^-}}{\text{mol CH}_3\text{COOH}}\right)} = 3.18 \times 10^{-5} \text{ mol } e^-$$

Charge passed in the second electrolyzer:

$$(3.18 \times 10^{-5} \text{ mol } e^-)\left(\frac{96485 \text{ C}}{\text{mol } e^-}\right) = 3.07$$

Moles of ethanol produced:

$$(3.18 \times 10^{-5} \text{ mol } e^-)(0.42)\left(\frac{\text{mol C}_2\text{H}_5\text{OH}}{8 \text{ mol } e^-}\right) = 1.67 \times 10^{-6} \text{ mol C}_2\text{H}_5\text{OH}$$

Faradaic efficiency for ethanol across the entire cascade system:

$$\frac{(1.67 \times 10^{-6} \text{ mol C}_2\text{H}_5\text{OH})\left(\frac{12 \text{ mol } e^-}{\text{mol C}_2\text{H}_5\text{OH}}\right)\left(\frac{96485 \text{ C}}{\text{mol } e^-}\right)}{(1 \text{ C}) + (3.07 \text{ C})} = 0.465 = 47.5\%$$

Average applied potential for the entire cascade system:

$$\frac{(-0.25 \text{ V})(1 \text{ C}) + (-0.3 \text{ V})(3.07 \text{ C})}{(1 \text{ C}) + (3.07 \text{ C})} = -0.29 \text{ V}$$

Example 3. Integrated Ethanol Cascade Electrolyzer Design

As shown in the calculations in Example 2, a sequential cascade affords many advantages for selectivity and minimal overpotential. These benefits are preferably realized when the intermediate products are transferred between reactors and converted at high yield. This is achieved through conventional chemical engineering methods such as separation processes. With reference to FIG. 1, a separator to remove CO from $H_2$ in the second electrolyzer gas output and recycle it back to the OD-Cu cathode gas input stream strongly increases the CO conversion and subsequent cascade performance. On an industrial scale, pressure swing adsorption is a viable cost-effective technology for achieving this separation.

An electrolyzer designed with a large foil catalyst area and minimal electrolyte volume also works well for maximum product detection sensitivity for diagnostic stages and characterizing the catalytic activity under individual electrolyzer operating conditions. However, in working towards an integrated industrial/commercial cascade design, high currents and high yield become more important. Two approaches to an integrated cascade electrolyzer are taken. In both designs, $CO_2$ is saturated in the first-stage electrolyte via an absorption column and then the electrolyte is cycled through the first-stage cathode to minimize the presence of $CO_2$ in the second stage. The aqueous 0.1 M $KHCO_3$ electrolyte is replaced with a dilute ionic liquid in water electrolyte. The low solubility of $CO_2$ in aqueous solution (38 mM at 25° C. and 1 atm) is a limiting factor in its electroreduction, with a diffusion-limited maximum current density of ~10 mA cm$^{-2}$ estimated for standard conditions. However, some ionic liquids (described elsewhere herein), have very high $CO_2$ solubility, and have been shown to greatly reduce the overpotential for $CO_2$ conversion to CO by lowering the free energy of the $CO_2$— intermediate. The electroreduction half reaction of $CO_2$ is coupled with water oxidation to be sustainable and scalable. Sustained high current density (>40 mA cm−2) for $CO_2$ electrolysis to CO at low overpotential in 96 mol % $H_2O$ and only 4 mol % 1-ethyl-3-methylimidazolium tetrafluoroborate (EMIM-BF4) ionic liquid is feasible. Ionic liquids are expensive, but their near-zero vapor pressure and inertness prevents their consumption in a cascade system and makes them feasible for commercial use. This affords an opportunity for a high performance cascade reaction system to make higher order products directly from CO2RR in an ionic liquid. CO solubility is low in the aqueous/ionic liquid mixture and the gas readily separates despite the high solubility of $CO_2$. Integrated reactor designs leverage this by directing the CO evolution from the first-stage catholyte immediately into the second-stage catholyte to minimize pass-through CO bubbles that could lower the conversion. The half-reactions of interest in both cases are shown below. $CO_2$ reduction and hydrocarbon formation occur via the half-reaction on the cathode, and the reaction is balanced by water oxidation at the anode. Due to the different pHs of these two reactions, the water oxidation proceeds through two different routes.

Electrolysis Stage 1:

Cathode: $2CO_2 + 4H^+ + 4e^- \rightarrow 2CO + 2H_2O$

Anode: $2H_2O \rightarrow O_2 + 4H^+ + 4e^-$

Total: $2CO_2 \rightarrow 2CO + O_2$

Electrolysis Stage 2:

Cathode: $2CO + 7H_2O + 8e^- \rightarrow C_2H_5OH + 8OH^-$

Anode: $8OH^- \rightarrow 4H_2O + 2O_2 + 8e^-$

Total: $2CO + 3H_2O \rightarrow C_2H_5OH + 2O_2$

Figure 12A:
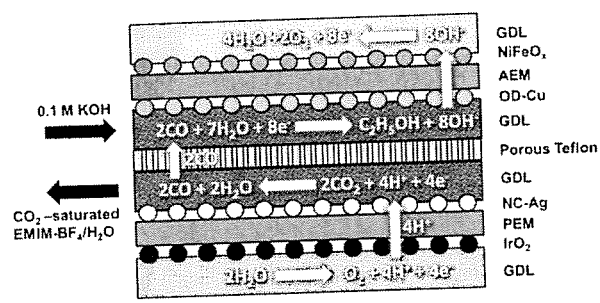
FIGS. 12A and B Dual-MEA integrated cascade electrolyzer design. (A) Dual-MEA cross section, and (B) exploded view with middle plate for porous Teflon membrane and contacting cathodes.
Figure 12B:
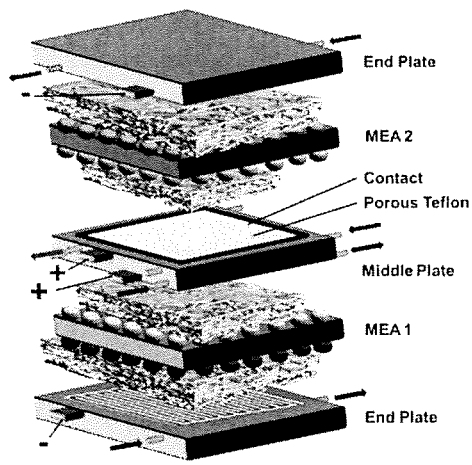

FIG. 12 shows a schematic for the active area of a dual membrane electrode assembly (MEA) integrated cascade electrolyzer. The compact design of an MEA, in which the cathode and anode electrocatalyst particles are contained at either surface of the membrane, minimizes ohmic resistance. On either side of the MEA, a highly porous gas diffusion layer (GDL) aids in mass transport of the reactants to the active catalyst sites and makes effective electrical contact to the catalyst. For the cathodes, this is e.g. common carbon Toray paper, and for the anodes a more chemically inert metal foam is used. Additional electrocatalyst particles are loaded onto the GDL layers to increase the current density. To connect the two stages of the cascade, a middle plate ring supports a porous Teflon membrane with gaskets for sealing, a metal lip to contact the inner GDL layers, and separate ports for electrolyte flow through the GDL on either side. Porous Teflon is chosen as the membrane between the two stages since it is chemically inert and prevents the passage of liquid while permitting the diffusion of volatile species. The Teflon membrane keeps the two electrolytes separate while allowing the direct transfer of CO to the second stage as it is generated. To increase conversion of the CO and maintain a closed loop for the ionic liquid, the output water/ionic liquid catholyte from the first stage is circulated back to the input flow through a $CO_2$ absorber. A flow rate of 0.1 M KOH in the second stage is independently optimized to achieve the best CO uptake and conversion. Additionally, flow of the second-stage catholyte, in contrast to a static catholyte, aids mass transfer and removes the ethanol as it is produced. A decreased residence time for ethanol in the cell reduces its further conversion to $C_{3+}$ species and permits higher and more stable $C_2H_5OH$ faradaic efficiency.

A second integrated cascade electrolyzer design, an interdigitated electrode cell, is shown in FIG. 13. In the interdigitated design, the first-stage catholyte flow takes a serpentine path across the entire cathode, providing the maximum opportunity to build CO concentration and drive diffusion to the second-stage catholyte. The second-stage catholyte flowing in the opposite direction ensures the best possible CO concentration gradient across the porous Teflon membrane through the cell area. The interdigitated electrodes are produced by evaporating Au on the end plate, followed by machine milling a serpentine groove to separate the first- and second-stage cathodes. Ag and Cu are then selectively electrodeposited on the first- and second-stage, respectively, before being further processed to Ag—NC and OD-Cu. The groove is then filled and sealed with a porous Teflon membrane wall between the interdigitated electrodes. The anode is produced in similar fashion but with an impermeable divider between the two electrodes. Again, the CO-rich first-stage catholyte is recycled for higher conversion and the second-stage catholyte is collected to prevent further reduction of the ethanol. A single Selemion anion exchange membrane (AEM) separates the two cells.

Additional modifications of the reactor design include spreading the intermediate CO gas flow to the second electrolyzer in smaller bubbles across a larger area OD-Cu cathode in a greater electrolyte volume. Alternatively, a separator to remove CO from $H_2$ in the second electrolyzer gas output and recycle it back to the OD-Cu cathode gas input stream is used and increases the CO conversion and subsequent cascade performance. On an industrial scale, pressure swing adsorption is a viable cost-effective technology for achieving this separation. When a recycle stream or modified reactor design allows complete conversion of the CO intermediate while maintaining the other system performance characteristics (80% faradaic efficiency for CO at −0.6 V vs. RHE in electrolyzer 1, 28.4% faradaic efficiency for $C_2H_5OH$ at −0.3 V vs. RHE in electrolyzer 2 with 7.4% faradaic efficiency for acetate, with the balance towards $H_2$), an overall cascade faradaic efficiency for $C_2H_5OH$ of 33.4% is attained at an average applied potential of −0.36 V vs. RHE. Furthermore, when state-of-the-art $CO_2$-to-CO (98% faradaic efficiency with Ag in ionic liquid at ~−0.25 V vs. RHE) and CO-to-$C_2H_5OH$ (42% faradaic efficiency for ethanol with 11% faradaic efficiency for acetate, with the balance towards $H_2$ with OD-Cu in 0.1 M KOH at −0.3 V vs. RHE) electrochemical conversion performance characteristics are combined with 100% CO conversion in a perfect recycle stream, an overall cascade faradaic efficiency of 47.5% is achieved with an average applied potential of −0.29 V vs. RHE (−380 mV overpotential).

For the present $CO_2$ to CO to $C_2H_5OH$ approach, a reactor design with separation and recycle streams to maximize the CO conversion and prevent further $C_2H_5OH$ reduction is predicted to enable a faradaic efficiency for ethanol from carbon dioxide up to 47.5% at an average cathodic overpotential <400 mV.

Example 4. Reactions with Other Reactants

Cascade electrolysis experiments with liquid phase reactants (i.e., ethanol, acetaldehyde, etc.) use a range of molarities (0.001-0.1 M). Slow-scan rate cyclic voltammetry measurements provide the current density vs. voltage (J-V) behavior for cathodic potentials between −2 to 0 V vs. RHE. The electrolyzer is run potentiostatically at 50 to 100 mV intervals in this region for ~60 min, with the headspace and liquid sampled every 15 min to correlate product quantification to applied bias. This same faradaic efficiency vs. potential behavior is measured in a two-electrode configuration for each individual stage of the integrated cascade prototypes to establish how the anode overpotential and cell resistance affects the product distribution vs. cell potential. This data establishes the ideal operating point for maximum $CO_2$ to CO and CO to $C_2H_5OH$ conversion in the absence of reference electrodes in the prototype reactors. Stability is evaluated by 2 h or greater galvanostatic measurements (monitoring changes in overpotential) and potentiostatic measurements at a potential that gives maximum desired product yield (monitoring changes to current density and faradaic efficiency of the desired product). For the ionic liquid electrolyte, 1-ethyl-3-methylimidazolium tetrafluoroborate (EMIM-BF4) is diluted in water.

Gas chromatography and nuclear magnetic resonance (NMR) will are used to determine where the electrons are going. As mentioned above, the gaseous headspace and a liquid aliquot are sampled at regular time intervals during potentiostatic measurements. An automated sample loop from the gas exhaust into a gas chromatograph (GC) with a thermal conductivity detector (TCD) and flame ionization detector (FID) in series identifies the gas products, and the resulting peaks are quantified by comparison to gas calibration standards. The liquid aliquots are analyzed via $^1$H NMR to identify and quantify the liquid products. Faradaic current efficiency is calculated by determining the number of coulombs required to produce the measured amount of each product and then dividing by the total charge passed during the sampling period, and subsequently averaging this number for each sampling at the same potential. The resulting data are used to identify potentials for optimal yield of the desired product under the cascade operating conditions.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A method of electrochemical conversion of $CO_2$ to a multi-carbon compound comprising:
    transferring $CO_2$ from a $CO_2$ source to a first reaction module via a first conduit that connects the $CO_2$ source to the first reaction module;
    in the first reaction module, reacting the $CO_2$ with water under first electrochemical reaction conditions sufficient to produce CO and hydroxide ions;
    transferring the CO to a second reaction module via a second conduit that connects the first reaction module and the second reaction module;
    in the second reaction module, reacting the CO with water under second electrochemical reaction conditions sufficient to produce the multi-carbon compound; and
    collecting the multi-carbon compound.

2. The method of claim 1, wherein the first electrochemical reaction conditions differ from the second electrochemical reaction conditions.

3. The method of claim 1, wherein the first electrochemical reaction conditions include the use of a first catalyst and the second electrochemical reaction conditions include the use of a second catalyst.

4. The method of claim 3, wherein the first catalyst and the second catalyst are different.

5. The method of claim 1, wherein the multi-carbon compound is a multi-carbon alcohol, a multi-carbon hydrocarbon, a multi-carbon aldehyde or a multi-carbon carboxylic acid.

6. The method of claim 5, wherein the multi-carbon alcohol is ethanol, propanol, or butanol.

7. The method of claim 5, wherein the multi-carbon hydrocarbon is ethylene.

8. The method of claim 5, wherein the multi-carbon aldehyde is acetaldehyde or propionaldehyde.

9. The method of claim 5, wherein the multi-carbon carboxylic acid is acetic acid or gamma-hydroxybutyric acid.

10. The method of claim 6, wherein the multi-carbon alcohol is ethanol; the first electrochemical reaction conditions include contacting the $CO_2$ and water with an Ag-based catalyst or an Au-based catalyst, and the second electrochemical reaction conditions include contacting the CO and water with an oxide-derived Cu catalyst, a nanostructured Cu catalyst or a heteroatomic carbon based catalyst.

11. The method of claim 10, wherein the Ag-based catalyst is Ag-nanocoral (Ag-NC).

12. The method of claim 10, wherein the oxide-derived Cu catalyst is an oxide-derived nanocrystalline copper complex (OD-Cu) catalyst.

13. A modular system for the electrochemical conversion of carbon dioxide to a multi-carbon alcohol, comprising:
    a first electrolyzer module comprising a first catalyst that catalyzes the conversion of $CO_2$ to CO;
    a second electrolyzer module comprising a second catalyst that catalyzes the conversion of CO to a multi-carbon compound; and
    a first conduit configured to transfer $CO_2$ from a $CO_2$ source to the first electrolyzer module; and
    a membrane configured to permit selective diffusion of the CO from the first electrolyzer module to the second electrolyzer module.

14. The modular system of claim 13, wherein the first and second catalysts are different.

15. The modular system of claim 13, wherein reaction conditions in the first electrolyzer module differ from reaction conditions in the second electrolyzer module.

16. The modular system of claim 13, wherein the first catalyst is an Ag-based catalyst or an Au-based catalyst, and the second catalyst is an oxide-derived Cu catalyst, a nanostructured Cu catalyst, a heteroatomic carbon-based catalyst or a doped nanodiamond-based catalyst.

17. The modular system of claim 16, wherein the Ag-based catalyst is an Ag-nanocoral (Ag-NC) catalyst.

18. The modular system of claim 16, wherein the oxide-derived Cu catalyst is an oxide-derived nanocrystalline copper complex (OD-Cu) catalyst.

19. The modular system of claim 13, further comprising a $CO_2$ absorption column operably connected to the first electrolyzer module, wherein the $CO_2$ absorption column supplies $CO_2$ to the first electrolyzer module.

20. The modular system of claim 13, further comprising a gas-liquid separator disposed between the first electrolyzer module and the second electrolyzer module, wherein the gas-liquid separator i) separates CO and electrolyte from a CO-electrolyte stream received from the first electrolyzer module; ii) transfers the CO to the second electrolyzer module; and e) transfers the electrolyte back to the first electrolyzer module.

21. The method of claim 1, wherein the step of reacting $CO_2$ with water is performed at a temperature of from 29-90° C. or at room temperature.

22. The modular system of claim 13, further comprising: one or more collection chambers; one or more filters; one or more valves; and/or one or more pumps.

23. The modular system of claim 13, wherein the first electrolyzer module comprises a first cathode and a first electrolyte configured to catalyze the conversion of $CO_2$ to CO; and the second electrolyzer module comprises a second cathode and a second electrolyte configured to catalyze the conversion of CO to a multi-carbon compound.

24. The method of claim 1 wherein the second conduit is a membrane that permits selective diffusion of the CO from the first electrolyzer module into the second electrolyzer module.

* * * * *